United States Patent [19]
Berkner et al.

[11] Patent Number: 6,039,944
[45] Date of Patent: Mar. 21, 2000

[54] MODIFIED FACTOR VII

[75] Inventors: Kathleen L. Berkner, Cleveland Heights, Ohio; Lars Christian Petersen, Hoersholm, Denmark; Charles E. Hart, Brier, Wash.; Ulla Hedner, Malmo, Sweden; Claus Bregengaard, Hellerup, Denmark

[73] Assignees: ZymoGenetics, Inc., Seattle, Wash.; Novo Nordisk A/S, Bagsvaerd, Denmark

[21] Appl. No.: 08/464,233

[22] Filed: Jun. 5, 1995

Related U.S. Application Data

[60] Division of application No. 08/327,690, Oct. 24, 1994, Pat. No. 5,817,788, which is a continuation-in-part of application No. PCT/US94/05779, May 23, 1994, and a continuation-in-part of application No. 08/065,725, May 21, 1993, abandoned, which is a continuation-in-part of application No. PCT/US92/01636, Feb. 28, 1992, and a division of application No. 07/662,920, Feb. 28, 1991, abandoned.

[51] Int. Cl.$^7$ .......................... A61K 36/36; A61K 38/48; C12N 9/48; C12N 9/64
[52] U.S. Cl. ...................... 424/94.64; 435/212; 435/226; 514/12; 514/822; 530/384
[58] Field of Search .............................. 424/94.63, 94.64; 435/212, 226; 514/12, 822; 530/384

[56] References Cited

U.S. PATENT DOCUMENTS

| | | | |
|---|---|---|---|
| 4,775,624 | 10/1988 | Bang et al. | 435/226 |
| 4,784,950 | 11/1988 | Hagen et al. | 435/69.6 |
| 4,829,052 | 5/1989 | Glover et al. | 514/12 |
| 4,959,318 | 9/1990 | Foster et al. | 435/172.3 |
| 4,994,371 | 2/1991 | Davie et al. | 435/6 |
| 5,190,919 | 3/1993 | Fair et al. | 514/15 |
| 5,278,144 | 1/1994 | Wolf | 514/12 |

FOREIGN PATENT DOCUMENTS

| | | |
|---|---|---|
| 255771 | 2/1988 | European Pat. Off. |
| 92/15686 | 9/1929 | WIPO |
| 86/06408 | 11/1986 | WIPO |
| 89/90612 | 10/1989 | WIPO |
| 90/03390 | 4/1990 | WIPO |
| 90/15619 | 12/1990 | WIPO |
| 91/11514 | 8/1991 | WIPO |

OTHER PUBLICATIONS

Nemerson et al., "An Assay for Coagulation Factor VII using Factor VII–depleted Bovine Plasma," *J. Lab. Clin. Med.*, 83:301–303 (1974).

A. Lehninger, ed., "The Molecular Basis of Cell Structure and Function", *Biochemistry* p. 220, 2d ed., Worth Publishers, Inc., New York 1975.

Radcliffe et al., "Mechanism of Activation of Bovine Factor VII", *J. Biol. Chem.* 251: 4797–4802 (1976).

Broze and Majerus, "Purification and Properties of Human Coagulation Factor VII", *J. Biol. Chem.* 255:1242–1247 (1980).

McRae et al., "Mapping the Active Sites of Bovine Thrombin, Factor IX$_a$, Factor X$_a$, Factor XI$_a$, Factor XII$_a$, Plasma Kallikrein, and Trypsin with Amino Acid and Peptide Thioesters: Development of New Sensitive Substrates" *Biochem.* 20: 7196–7206 (1981).

Degen et al., "Characterization of the Complementary Deoxyribonucleic Acid and Gene Coding for Human Prothrombin", *Biochem.* 22:2087–2097 (1983).

Cho et al., "Active–Site Mapping of Bovine and Human Blood Coagulation Serine Proteases Using Synthetic Peptide 4–Nitroanilide and Thio Ester Substrates", *Biochem.*, 23: 644–650 (1984).

Zoller et al., *DNA* 3(6):479–488 (1984).

Leytus et al., "Gene of Human Factor X: A Blood Coagulation Factor Whose Gene Organization is Essentially Identical with That of Factor IX and Protein C", *Biochem.* 25:5098–5102 (1986).

Nemerson, "An Ordered Addition, Essential Activation Model of the Tissue Factor Pathway of Coagulation: Evidence for a Conformational Cage", *Biochem.* 25:4020–4033 (1986).

Foster et al., "Propeptide of Human Protein C is Necessary for γ–Carboxylation" *Biochem.* 26: 7003–7011 (1987).

Thim et al., "Amino Acid Sequence and Posttranslational Modifications of Human Factor VII$_a$ from Plasma and Transfected Baby Hamster Kidney Cells", *Biochem.* 27:7785–7793 (1988).

Takeya et al., "Bovine Factor VII, Its Purification and Complete Amino Acid Sequence", *J. Biol. Chem.* 263: 14868–14872 (Oct., 1988).

Sakai et al., "Binding of Human Factors VII and VIIa to a Human Bladder Carcinomas Cell Line (J82)", *J. Biol. Chem.* 264:9980–9988 (1989).

Hatton et al., "Deendothelialization in Vivo Initiates a Thrombogenic Reaction at the Rabbit Aorta Surface", *Am. J. Pathol.* 135:499–508 (Sep., 1989).

Rapaport, "Inhibition of Factor VIIa/Tissue Factor–Induced Blood Coagulation: With Particular Emphasis Upon a Factor Xa–Dependent Inhibitory Mechanism" *Blood* 73(2):359–365 (Feb. 1989).

Wildgoose et al., "Synthesis, Purification and Characterization of an Arg$_{152}$→Glu Site–Directed Mutant of Recombinant Human Blood Clotting Factor VII", *Biochem.* 29:3413–3420 (1990).

(List continued on next page.)

*Primary Examiner*—Dian C. Jacobson
*Attorney, Agent, or Firm*—Townsend and Townsend and Crew LLP

[57] ABSTRACT

The catalytic active site of Factor VII is modified to produce a compound which effectively interrupts the blood coagulation cascade. The modifications render Factor VIIa substantially unable to activate plasma Factors X or IX. Pharmaceutical compositions of the modified Factor VII are used to treat a variety of coagulation-related disorders.

19 Claims, 3 Drawing Sheets

OTHER PUBLICATIONS

Sarembock et al., "Effectiveness of Recombinant Desulphatohirudin in Reducing Restenosis After Balloon Angioplasty of Atherosclerotic Femoral Arteries in Rabbits", *Circulation* 84:232–243 (Jul. 1991).

Wilcox "Thrombin and Other Potential Mechanisms Underlying Restenosis", *Circulation* 84:432–435 (Jul., 1991).

LeBonniec et al., "The Role of Calcium Ions in Factor X Activation by Thrombin E192Q" *J. Biol. Chem.* 267:6970–6976 (Apr., 1992).

Jang et al., "Antithrombotic Effect of a Monoclonal Antibody Against Tissue Factor in a Rabbit Model of Platelet–Mediated Arterial Thrombosis", *Arterio. & Thromb.* 12:948–954 (Aug., 1992).

Loscalzo, "The Relation Between Atherosclerosis and Thrombosis", *Circulation* 86: III–95–99 (Dec., 1992).

Marmur et al., "Tissue Factor is Rapidly Induced in Arterial Smooth Muscle after Balloon Injury", *J. Clin. Invest.* 91:2253–2259 (May, 1993).

Hanson, "Intraluminal Drug Delivery for Experimental Thrombosis and Restenosis", *Restenosis Summit V,* pp. 296–300.

MODIFIED FACTOR VII

This application is a divisional of Ser. No. 08/327,690, filed Oct. 24, 1994, now U.S. Pat. No. 5,817,788, which is a continuation-in-part of PCT/US94/05779, filed May 23, 1994, and a continuation-in-part of Ser. No. 08/065,725, filed May 21, 1993, now abandoned, which is a continuation-in-part of PCT/US92/01636, filed Feb. 28, 1992 and a divisional of Ser. No. 07/662,920, filed Feb. 28, 1991, abandoned and now Ser. No. 08/164,666, now abandoned, each of which is expressly incorporated herein in its entirety by reference.

FIELD OF THE INVENTION

The present invention relates to proteins useful as anticoagulants. More specifically, the present invention relates to modified forms of Factor VII that inhibit blood coagulation and tissue factor.

BACKGROUND OF THE INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors that have undergone such a conversion and generally referred to as "active factors," and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilization of factors present only in plasma. A series of protease-mediated activations ultimately generates Factor IXa which, in conjunction with Factor VIIIa, cleaves Factor X into Xa. An identical proteolysis is effected by Factor VIIa and its co-factor, tissue factor, in the "extrinsic pathway" of blood coagulation. Tissue factor is a membrane bound protein and does not normally circulate in plasma. Upon vessel disruption, however, it can complex with Factor VIIa to catalyze Factor X activation or Factor IX activation in the presence of Ca++ and phospholipid (Nemerson and Gentry, *Biochem.* 25:4020–4033 (1986)). While the relative importance of the two coagulation pathways in hemostasis is unclear, in recent years Factor VII and tissue factor have been found to play a pivotal role in the regulation of blood coagulation.

Factor VII is a trace plasma glycoprotein that circulates in blood as a single-chain zymogen. The zymogen is catalytically inactive (Williams et al., *J. Biol. Chew.* 264:7536–7543 (1989); Rao et al., *Proc. Natl. Acad. Sci. USA.* 85:6687–6691 (1988)). Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in hemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at $Arg_{152}$-$Ile_{153}$ (Hagen et al., *Proc. Natl. Acad. Sci. USA* 83: 2412–2416 (1986); Thim et al., *Biochem.* 27:7785–7793 (1988) both of which are incorporated herein by references). Bovine factor VII is activated by cleavage at the analogous $Arg_{152}$-$Ile_{153}$ bond (Takeya et al., *J. Biol. Chem.* 263: 14868–14877, 1988). In the presence of tissue factor, phospholipids and calcium ions, the two-chain Factor VIIa rapidly activates Factor X or Factor IX by limited proteolysis.

It is often necessary to selectively block the coagulation cascade in a patient. Anticoagulants such as heparin, coumarin, derivatives of coumarin, indandione derivatives, or other agents may be used, for example, during kidney dialysis, or to treat deep vein thrombosis, disseminated intravascular coagulation (DIC), and a host of other medical disorders. For example, heparin treatment or extracorporeal treatment with citrate ion (U.S. Pat. No. 4,500,309) may be used in dialysis to prevent coagulation during the course of treatment. Heparin is also used in preventing deep vein thrombosis in patients undergoing surgery.

Treatment with heparin and other anticoagulants may, however, have undesirable side effects. Available anticoagulants generally act throughout the body, rather than acting specifically at a clot site. Heparin, for example, may cause heavy bleeding. Furthermore, with a half-life of approximately 80 minutes, heparin is rapidly cleared from the blood, necessitating frequent administration. Because heparin acts as a cofactor for antithrombin III (AT III), and AT III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al. (U.S. Pat. No. 4,732,891) disclose human placenta-derived anticoagulant proteins. In addition, AT III has been proposed as a therapeutic anticoagulant (Schipper et al., Lancet 1 (8069): 854–856 (1978); Jordan, U.S. Pat. No. 4,386,025; Bock et al., U.S. Pat. No. 4,517,294).

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC proliferation and migration into the intima, which characteristically occurs within the first few weeks and up to six months after injury and stops when the overlying endothelial layer is reestablished.

In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

There is still a need in the art for improved compositions having anticoagulant activity which can be administered at relatively low doses and do not produce the undesirable side effects associated with traditional anticoagulant compositions. The present invention fulfills this need by providing anticoagulants that act specifically at sites of injury, and further provides other related advantages.

SUMMARY OF THE INVENTION

Novel compositions which comprise modified Factor VII having anticoagulant properties are provided. The modified Factor VII compositions also inhibit tissue factor. The Factor VII sequence has at least one amino acid modification, where the modification is selected so as to substantially reduce the ability of activated Factor VII to catalyze the activation of plasma Factors X or IX, and thus is capable of inhibiting clotting activity. The novel Factor VII has an active site modified by at least one amino acid substitution, and in its modified form is capable of binding tissue factor. The modified Factor VII compositions are typically in substantially pure form.

The compositions of the invention are particularly useful in methods for treating patients when formulated into pharmaceutical compositions, where they may be given to individuals suffering from a variety of disease states to treat coagulation-related conditions. Such modified Factor VII molecules, capable of binding tissue factor but having a substantially reduced ability to catalyze activation of other factors in the clotting cascade, may possess a longer plasma half-life and thus a correspondingly longer period of anti-coagulative activity when compared to other anticoagulants. Among the medical indications for the subject compositions are those commonly treated with anticoagulants, such as, for example, deep vein thrombosis, pulmonary embolism, stroke, disseminated intravascular coagulation (DIC), fibrin deposition in lungs and kidneys associated with gram-negative endotoxemia, and myocardial infarction. The compositions can be used to inhibit vascular restenosis as occurs following mechanical vascular injury, such as injury caused by balloon angioplasty, endarterectomy, reductive atherectomy, stent placement, laser therapy or rotablation, or as occurs secondary to vascular grafts, stents, bypass grafts or organ transplants. The compositions can thus be used to inhibit platelet deposition and associated disorders. Thus, a method of inhibiting coagulation, vascular restenosis or platelet deposition, for example, comprises administering to a patient a composition comprising modified Factor VII, such as that having at least one amino acid substitution in a catalytic triad of $Ser_{344}$, $Asp_{242}$ and $His_{193}$, in an amount sufficient to effectively inhibit coagulation, vascular restenosis or platelet deposition. The methods also find use in the treatment of acute closure of a coronary artery in an individual, which comprises administering the modified Factor VII in conjunction with tissue plasminogen activator or streptokinase.

Typically, for administration to humans the pharmaceutical compositions will comprise modified human Factor VII protein and pharmaceutically-acceptable carriers and buffers.

In preferred embodiments of human and bovine Factor VII, the active site residue $Ser_{344}$ is modified, replaced with Gly, Met, Thr, or more preferably, Ala. Such substitution could be made separately or in combination with substitution(s) at other sites in the catalytic triad, which includes $His_{193}$ and $Asp_{242}$.

In another aspect the invention relates to a polynucleotide molecule comprising two operatively linked sequence coding regions encoding, respectively, a pre-pro peptide and a gla domain of a vitamin K-dependent plasma protein, and a gla domain-less Factor VII protein, wherein upon expression said polynucleotide encodes a modified Factor VII molecule which does not significantly activate plasma Factors X or IX, and is capable of binding tissue factor. The modified Factor VII molecule expressed by this polynucleotide is a biologically active anticoagulant, that is, it is capable of inhibiting the coagulation cascade and thus the formation of a fibrin deposit or clot. To express the modified Factor VII the polynucleotide molecule is transfected into mammalian cell lines, such as, for example, BHK, BHK 570 or 293 cell lines.

DESCRIPTION OF THE SPECIFIC EMBODIMENTS

Figure 1:
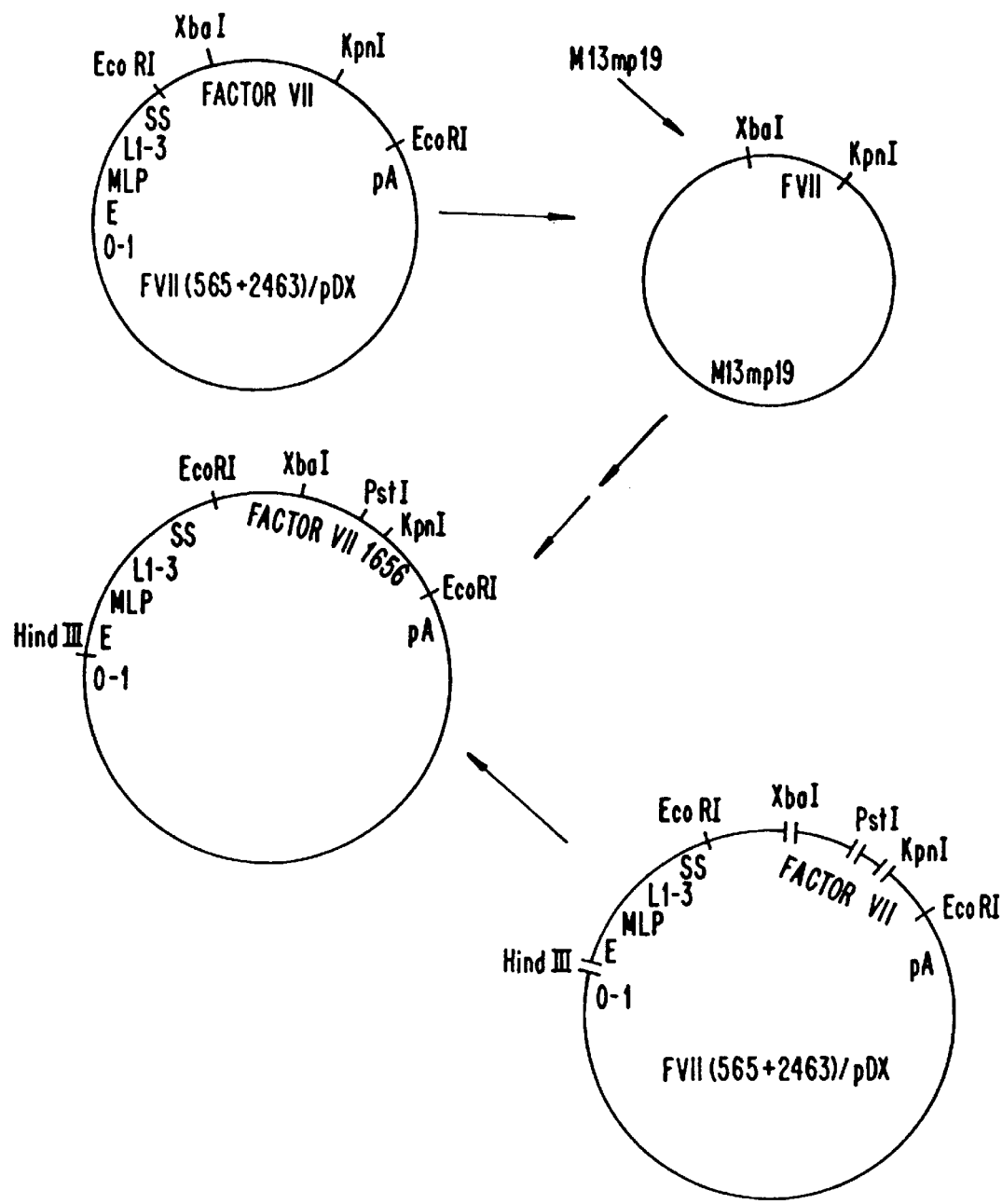
FIG. 1 illustrates the construction of an expression vector for a $Ser_{344} \rightarrow Ala$ modified Factor VII DNA sequence. Symbols used include 0-1, the 0-1 map unit sequence from adenovirus 5; E, the SV40 enhancer; MLP, the adenovirus 2 major late promotor; SS, a set of splice sites; and pA, the polyadenylation signal from SV40 in the late orientation.

Novel modified Factor VII having anticoagulant activity is provided by the present invention. The modified Factor VII can be in the form of the zymogen (i.e., a single-chain molecule) or can be cleaved at its activation site. Thus, by "modified Factor VII" is meant to include modified Factor VII and modified Factor VIIa molecules that bind tissue factor and inhibit the activation of Factor IX to IXa and Factor X to Xa. Compositions of the modified Factor VII are suitable for administration to a variety of mammals, particularly humans, to inhibit the coagulation cascade. Modified Factor VII may be administered to a patient in conjunction with or in place of other anticoagulant compounds.

Factor VII plays an important role in the coagulation cascade, particularly that involving the extrinsic pathway. Present in the circulating plasma as an inactive single chain zymogen protein, once activated, Factor VIa, in combination with tissue factor and calcium ions, activates Factor X to Xa and activates Factor IX to IXa, with the eventual formation of a fibrin clot.

The present invention provides the ability to inhibit this sequence of events in the coagulation cascade by preventing or otherwise inhibiting the activation of Factors X and IX by Factor VIIa. Factor VII proteins of the invention have a catalytic site which is modified to decrease the catalytic activity of Factor VIIa, while the molecule retains the ability to bind to tissue factor. The modified Factor VII molecules compete with native Factor VII and/or VIIa for binding to tissue factor. As a result, the activation of Factors X and IX is inhibited.

In one aspect of the present invention the catalytic activity of Factor VIIa is inhibited by chemical derivatization of the catalytic center, or triad. Derivatization may be accomplished by reacting Factor VII with an irreversible inhibitor such as an organophosphor compound, a sulfonyl fluoride, a peptide halomethyl ketone or an azapeptide, or by acylation, for example. Preferred peptide halomethyl ketones include PPACK (D-Phe-Pro-Arg chloromethyl-ketone; see U.S. Pat. No. 4,318,904, incorporated herein by reference), D-Phe-Phe-Arg chloromethylketone; and DEGRck (dansyl-GlU-Gly-Arg chloromethylketone).

In another aspect, the catalytic activity of Factor VIIa can also be inhibited by substituting, inserting or deleting amino acids. In preferred embodiments amino acid substitutions are made in the amino acid sequence of the Factor VII catalytic triad, defined herein as the regions which contain the amino acids which contribute to the Factor VIIa catalytic site. The substitutions, insertions or deletions in the catalytic triad are generally at or adjacent to the amino acids which form the catalytic site. In the human and bovine Factor VII proteins, the amino acids which form a catalytic "triad" are $Ser_{344}$, $Asp_{242}$, and $His_{193}$ (subscript numbering indicating position in the sequence). The catalytic sites in Factor VII from other mammalian species may be determined using presently available techniques including, among others, protein isolation and amino acid sequence analysis. Catalytic sites may also be determined by aligning a sequence with the sequence of other serine proteases, particularly chymotrypsin, whose active site has been previously determined (Sigler et al., *J. Mol. Biol.*, 35:143–164 (1968), incorporated herein by reference), and therefrom determining from said alignment the analogous active site residues.

The amino acid substitutions, insertions or deletions are made so as to prevent or otherwise inhibit activation by the Factor VIa of Factors X and/or IX. The Factor VII so modified should, however, also retain the ability to compete with authentic Factor VII and/or Factor VIIa for binding to tissue factor in the coagulation cascade. Such competition may readily be determined by means of, e.g., a clotting assay as described herein, or a competition binding assay using, e.g., a cell line having cell-surface tissue factor, such as the human bladder carcinoma cell line J82 (Sakai et al. *J. Biol. Chem.* 264: 9980–9988 (1989), incorporated by reference herein.) The amino acids which form the catalytic site in Factor VII, such as $Ser_{344}$, $Asp_{242}$, and $His_{193}$ in human and bovine Factor VII, may either be substituted or deleted. Within the present invention, it is preferred to change only a single amino acid, thus minimizing the likelihood of increasing the antigenicity of the molecule or inhibiting its ability to bind tissue factor, however two or more amino acid changes (substitutions, additions or deletions) may be made and combinations of substitution(s), addition(s) and deletions) may also be made. In a preferred embodiment for human and bovine Factor VII, $Ser_{344}$ is preferably substituted with Ala, but Gly, Met, Thr or other amino acids can be substituted. It is preferred to replace Asp with Glu and to replace His with Lys or Arg. In general, substitutions are chosen to disrupt the tertiary protein structure as little as possible. The model of Dayhoff et al. (in *Atlas of Protein Structure* 1978, Nat'l Biomed. Res. Found., Washington, D.C.), incorporated herein by reference, may be used as a guide in selecting other amino acid substitutions. One may introduce residue alterations as described above in the catalytic site of appropriate Factor VII sequence of human, bovine or other species and test the resulting protein for a desired level of inhibition of catalytic activity and resulting anticoagulant activity as described herein. For the modified Factor VII the catalytic activity will be substantially inhibited, generally less than about 5% of the catalytic activity of wild-type Factor VII of the corresponding species, more preferably less than about 1%.

The proteins of the present invention may be produced through the use of recombinant DNA techniques. In general, a cloned wild-type Factor VII DNA sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known. See U.S. Pat. No. 4,784,950, which is incorporated herein by reference, where the cloning and expression of recombinant human Factor VII is described. The bovine Factor VII sequence is described in Takeya et al., *J. Biol. Chem*, 263:14868–14872 (1988), which is incorporated by reference herein.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479–488, 1984). Thus, using the nucleotide and amino acid sequences of Factor VII, one may introduce the alterations) of choice.

The Factor VII modified according to the present invention includes those proteins that have the amino-terminal portion (gla domain) substituted with a gla domain of one of the vitamin K-dependent plasma proteins Factor IX, Factor X, prothrombin, protein C, protein S or protein Z. The gla domains of the vitamin K-dependent plasma proteins are characterized by the presence of gamma-carboxy glutamic acid residues and are generally from about 30 to about 40 amino acids in length with C-termini corresponding to the positions of exon-intron boundaries in the respective genes. Methods for producing Factor VII with a heterologous gla domain are disclosed in U.S. Pat. No. 4,784,950, incorporated by reference herein.

DNA sequences for use within the present invention will typically encode a pre-pro peptide at the amino-terminus of the Factor VII protein to obtain proper post-translational processing (e.g. gamma-carboxylation of glutamic acid residues) and secretion from the host cell. The pre-pro peptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the modified Factor VII where those modifications do not significantly impair the ability of the protein to act as an anticoagulant. For example, the Factor VII modified in the catalytic triad can also be modified in the activation cleavage site to inhibit the conversion of zymogen Factor VII into its activated two-chain form, as generally described in U.S. Pat. No. 5,288,629, incorporated herein by reference.

Expression vectors for use in carrying out the present invention will comprise a promoter capable of directing the transcription of a cloned gene or cDNA. Preferred promoters for use in cultured mammalian cells include viral promoters and cellular promoters. Viral promoters include the SV40 promoter (Subramani et al., *Mol. Cell. Diol.* 1:854–864, 1981) and the CMV promoter (Boshart et al., *Cell* 41:521–530, 1985). A particularly preferred viral promoter is the major late promoter from adenovirus 2 (Kaufman and Sharp, *Mol. Cell. Biol*, 2:1304–1319, 1982). Cellular promoters include the mouse kappa gene promoter (Bergman et al., *Proc. Natl. Acad. Sci. USA* 81:7041–7045, 1983) and the mouse $V_H$ promoter (Loh et al., *Cell* 33:85–93, 1983). A particularly preferred cellular promoter is the mouse metallothionein-I promoter (Palmiter et al., *Science* 222:809–814, 1983). Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nuc. Acids Res.* 9:3719–3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., *Cell* 14:725–732, 1978; Corsaro and Pearson, *Somatic Cell Genetics* 7:603–616, 1981; Graham and Van der Eb, *Virology* 52d:456–467, 1973) or electroporation (Neumann et al., *EMBO J.* 1:841–845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (*Mammalian Cell Technology*, Butterworth Publishers, Stoneham, Mass., incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1–2 days, to begin expressing the gene of interest. As used herein the term "appropriate growth medium" means a medium containing nutrients and other components required for the growth of cells and the expression of the modified Factor VII gene. Media generally include a carbon source, a nitrogen source, essential amino acids, essential sugars, vitamins, salts, phospholipids, protein and growth factors. For production of gamma-carboxylated modified Factor VII, the medium will contain vitamin K, preferably at a concentration of about 0.1 μg/ml to about 5 μg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of modified Factor VII.

Preferred mammalian cell lines for use in the present invention include the COS-1 (ATCC CRL 1650), baby hamster kidney (BHK) and 293 (ATCC CRL 1573; Graham et al., *J. Gen. Virol.* 36:59–72, 1977) cell lines. A preferred BHK cell line is the tk⁻ ts13 BHK cell line (Waechter and Baserga, *Proc. Natl. Acad. Sci. USA* 79:1106–1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216–4220, 1980).

Within the present invention, transgenic animal technology may be employed to produce modified Factor VII. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (typically from about 1 to 15 g/l). From a commercial point of view, it is clearly preferable to use as the host a species that has a large milk yield. While smaller animals such as mice and rats can be used (and are preferred at the proof of principle stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene. See Whitelaw et al., *Biochem J*. 286: 31–39 (1992). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836–840 (1988); Palmiter et al., *Proc. Natl. Acad. Sci. USA* 88: 478–482 (1991); Whitelaw et al., *Transgenic Res*. 1: 3–13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the modified Factor VII sequence is replaced with corresponding sequences from a milk specific protein gene. Such replacement provides a putative tissue-specific initiation environment to enhance expression. It is convenient to replace the entire modified Factor VII pre-pro and 5' non-coding sequences with those of, for example, the BLG gene, although smaller regions may be replaced.

For expression of modified Factor VII in transgenic animals, a DNA segment encoding modified Factor VII is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein. See, for example, von Heinje, *Nuc. Acids Res*. 14: 4683–4690 (1986); and Meade et al., U.S. Pat. No. 4,873,316, which are incorporated herein by reference.

Construction of expression units for use in transgenic animals is conveniently carried out by inserting a modified Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a modified Factor VII polypeptide, thereby creating a gene fusion that includes the expression control sequences of the milk protein gene. In any event, cloning of the expression units in plasmids or other vectors facilitates the amplification of the modified Factor VII sequence. Amplification is conveniently carried out in bacterial (e.g. *E. coli*) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468–1474 (1988)) or site-directed integration using embryonic stem (ES) cells (reviewed by Bradley et al., *Bio/Technology* 10: 534–539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., Manipulating the Mouse Embryo: A Laboratory Manual, Cold Spring Harbor Laboratory, 1986; Simons et al., *Bio/Technology* 6: 179–183 (1988); Wall et al., *Biol. Reprod*. 32: 645–651 (1985); Buhler et al., *Bio/Technology* 8: 140–143 (1990); Ebert et al., *Bio/Technology* 9: 835–838 (1991); Krimpenfort et al., *Bio/Technology* 9: 844–847 (1991); Wall et al., *J. Cell. Biochem*. 49: 113–120 (1992); U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380–7384 (1980); Gordon and Ruddle, *Science* 214: 1244–1246 (1981); Palmiter and Brinster, *Cell* 41: 343–345 (1985); Brinster et al., *Proc. Natl. Acad. Sci. USA* 82: 4438–4442 (1985); and Hogan et al. (ibid.). These techniques were subsequently adapted for use with larger animals, including livestock species (see e.g., WIPO publications WO 88/00239, WO 90/05188, and WO 92/11757; and Simons et al., *Bio/Technology* 6: 179–183 (1988). To summarize, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed. Production in transgenic plants may also be employed. Expression may be generalized or directed to a particular organ, such as a tuber. See, Hiatt, *Nature* 344:469–479 (1990); Edelbaum et al., *J. Interferon Res*. 12:449–453 (1992); Sijmons et al., *Bio/Technology* 8:217–221 (1990); and European Patent Office Publication EP 255,378.

Modified Factor VII produced according to the present invention may be purified by affinity chromatography on an anti-Factor VII antibody column. The use of calcium-dependent monoclonal antibodies, as described by Wakabayashi et al., *J. Biol. Chem*, 261:11097–11108, (1986) and Thim et al., *Biochem*. 27: 7785–7793, (1988), incorporated by reference herein, is particularly preferred. Additional purification may be achieved by conventional chemical purification means, such as high performance liquid chromatography. Other methods of purification, including barium citrate precipitation, are known in the art, and may be applied to the purification of the novel modified Factor VII described herein (see, generally, Scopes, R., *Protein Purification*, Springer-Verlag, N.Y., 1982). Substantially pure modified Factor VII of at least about 90 to 95% homogeneity is preferred, and 98 to 99% or more homogeneity most preferred, for pharmaceutical uses. Once purified, partially or to homogeneity as desired, the modified Factor VII may then be used therapeutically.

Within one embodiment of the invention the modified Factor VII is cleaved at its activation site to convert it to its two-chain form. Activation may be carried out according to procedures known in the art, such as those disclosed by Osterud, et al., *Biochemistry* 11:2853–2857 (1972); Thomas, U.S. Pat. No. 4,456,591; Hedner and Kisiel, *J. Clin. Invest.* 71:1836–1841 (1983); or Kisiel and Fujikawa, *Behring Inst. Mitt.* 73:29–42 (1983), which are incorporated herein by reference. The resulting molecule is then formulated and administered as described below.

The modified Factor VII molecules of the present invention and pharmaceutical compositions thereof are particularly useful for administration to humans to treat a variety of conditions involving intravascular coagulation. For example, although deep vein thrombosis and pulmonary embolism can be treated with conventional anticoagulants, the modified Factor VII described herein may be used to prevent the occurrence of thromboembolic complications in identified high risk patients, such as those undergoing surgery or those with congestive heart failure. In addition, modified Factor VII may act as an antagonist for tissue factor-mediated induction of coagulation, thus blocking the production of thrombin and the subsequent deposition of fibrin. As such, modified Factor VII may be useful for inhibiting tissue factor activity resulting in, for example, the inhibition of blood coagulation, thrombosis or platelet deposition.

The modified Factor VII molecules of the present invention may be particularly useful in the treatment of intimal hyperplasia or restenosis due to acute vascular injury. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, atherectomy, vascular graft emplacement or the like are employed. Hyperplasia may also occur as a delayed response in response to, e.g., graft emplacement or organ transplantation. Since modified Factor VII is more selective than heparin, generally binding only tissue factor which has been exposed at sites of injury, and because modified Factor VII does not destroy other coagulation proteins, it will be more effective and less likely to cause bleeding complications than heparin when used prophylactically for the prevention of deep vein thrombosis. The dose of modified Factor VII for prevention of deep vein thrombosis is in the range of about 50 $\mu$g to 500 mg/day, more typically 1 mg to 200 mg/day, and more preferably 10 to about 175 mg/day for a 70 kg patient, and administration should begin at least about 6 hours prior to surgery and continue at least until the patient becomes ambulatory. The dose of modified Factor VII in the treatment for restenosis will vary with each patient but will generally be in the range of those suggested above.

Recent advances in the treatment of coronary vascular disease include the use of mechanical interventions to either remove or displace offending plaque material in order to re-establish adequate blood flow through the coronary arteries. Despite the use of multiple forms of mechanical interventions, including balloon angioplasty, reduction atherectomy, placement of vascular stents, laser therapy, or rotoblator, the effectiveness of these techniques remains limited by an approximately 40% restenosis rate within 6 months after treatment.

Restenosis is thought to result from a complex interaction of biological processes including platelet deposition and thrombus formation, release of chemotactic and mitogenic factors, and the migration and proliferation of vascular smooth muscle cells into the intima of the dilated arterial segment.

The inhibition of platelet accumulation at sites of mechanical injury can limit the rate of restenosis in human subjects. Therapeutic use of a monoclonal antibody to platelet GpIIb/IIIa is able to limit the level of restenosis in human subjects (Califf et al., *N. Engl. J. Med.*, 330:956–961 (1994)). The antibody is able to bind to the GpIIb/IIIa receptor on the surfaces of platelets and thereby inhibit platelet accumulation. This data suggests that inhibition of platelet accumulation at the site of mechanical injury in human coronary arteries is beneficial for the ultimate healing response that occurs. While platelet accumulation occurs at sites of acute vascular injuries, the generation of thrombin at these sites may be responsible for the activation of the platelets and their subsequent accumulation.

As shown in the examples that follow, the modified Factor VII of the present invention is able to bind to cell-surface tissue factor. For example, DEGR-Factor VIIa binds cell-surface tissue factor with an equivalent or higher affinity than wild-type Factor VIIa. DEGR-Factor VIIa, however, has no enzymatic activity, yet it binds to tissue factor and acts as a competitive antagonist for wild-type Factor VIa, thereby inhibiting the subsequent steps in the extrinsic pathway of coagulation leading to the generation of thrombin.

Modified Factor VII molecules of the present invention which maintain tissue factor binding inhibit platelet accumulation at the site of vascular injury by blocking the production of thrombin and the subsequent deposition of fibrin.

Due to the ability of DEGR-Factor VII to block thrombin generation and limit platelet deposition at sites of acute vascular injury, modified Factor VII molecules which maintain tissue factor binding activity but lack Factor VIIa enzymatic activity can be used to inhibit vascular restenosis.

Thus, the compositions and methods of the present invention have a wide variety of uses. For example, they are useful in preventing or inhibiting restenosis following intervention, typically mechanical intervention, to either remove or displace offending plaque material in the treatment of coronary or peripheral vascular disease, such as in conjunction with and/or following balloon angioplasty, reductive atherectomy, placement of vascular stents, laser therapy, rotoblation, and the like. The compounds will is typically be administered within about 24 hours prior to performing the intervention, and for as much as 7 days or more thereafter. Administration can be by a variety of routes as further described herein. The compounds of the present invention can also be administered systemically or locally for the placement of vascular grafts (e.g., by coating synthetic or modified natural arterial vascular grafts), at sites of anastomosis, surgical endarterectomy (typically carotid artery endarterectomy), bypass grafts, and the like. The modified Factor VII and VIIa also finds use in inhibiting intimal hyperplasia and accelerated atherosclerosis associated with organ transplantation.

In the treatment of established deep vein thrombosis and/or pulmonary embolism, the dose of modified Factor VII ranges from about 50 µg to 500 mg/day, more typically 1 mg to 200 mg/day, and more preferably 10 mg to about 175 mg/day for a 70 kg patient as loading and maintenance doses, depending on the weight of the patient and the severity of the condition. Because of the lower likelihood of bleeding complications from modified Factor VII infusions, modified Factor VII can replace or lower the dose of heparin during or after surgery in conjunction with thrombectomies or embolectomies.

The modified Factor VII compositions of the present invention will also have substantial utility in the prevention of cardiogenic emboli and in the treatment of thrombotic strokes. Because of its low potential for causing bleeding complications and its selectivity, modified Factor VII can be given to stroke victims and may prevent the extension of the occluding arterial thrombus. The amount of modified Factor VII administered will vary with each patient depending on the nature and severity of the stroke, but doses will generally be in the range of those suggested below.

Pharmaceutical compositions of modified Factor VII provided herein will be a useful treatment in acute myocardial infarction because of the ability of modified Factor VII to inhibit in vivo coagulation. Modified Factor VII can be given as an adjuvant with tissue plasminogen activator or streptokinase during the acute phases of the myocardial infarction. In acute myocardial infarction, the patient is given a loading dose of at least about 50 µg to 500 mg/day, more typically 1 mg to 200 mg/day, and more preferably 10 mg to about 175 mg/day for a 70 kg patient as loading and maintenance doses.

The modified Factor VII of the present invention is useful in the treatment of disseminated intravascular coagulation (DIC) and other conditions associated with gram-negative bacteremia. Patients with DIC characteristically have widespread microcirculatory thrombi and often severe bleeding problems which result from consumption of essential clotting factors. Because of its selectivity, modified Factor VII will not aggravate the bleeding problems associated with DIC, as do conventional anticoagulants, but will retard or inhibit the formation of additional microvascular fibrin deposits. Thus, the modified Factor VII of the invention, including the DEGR-Factor VII and DEGR-VIIa, is useful in the inhibition of fibrin deposition associated with endotoxemia and endotoxin shock and thus also moderates effects associated with gram-negative bacteremia. The DEGR-Factor VIIa has been shown in rabbits to demonstrate a dose-response effect for blocking fibrin deposition in kidneys and lungs, and in baboons to prolong survival of treated animals. In cases of acute bacteremia, endotoxemia or DIC, the patient is given a loading dose of at least about 50 µg to 500 mg/day, more typically 1 mg to 200 mg/day, and more preferably 10 mg to about 175 mg/day for a 70 kg patient, with maintenance doses thereafter in the range of 50 µg to 500 mg/day, typically 1 mg to 200 mg/day for a 70 kg patient.

The pharmaceutical compositions are intended for parenteral, topical or local administration for prophylactic and/or therapeutic treatment. Preferably, the pharmaceutical compositions are administered parenterally, i.e., intravenously, subcutaneously, or intramuscularly. Thus, this invention provides compositions for parenteral administration which comprise a solution of the modified Factor VII molecules dissolved in an acceptable carrier, preferably an aqueous carrier. A variety of aqueous carriers may be used, e.g., water, buffered water, 0.4% saline, 0.3% glycine and the like. The modified Factor VII molecules can also be formulated into liposome preparations for delivery or targeting to sites of injury. Liposome preparations are generally described in, e.g., U.S. Pat. No. 4,837,028, U.S. Pat. No. 4,501,728, and U.S. Pat. No. 4,975,282, incorporated herein by reference. The compositions may be sterilized by conventional, well known sterilization techniques. The resulting aqueous solutions may be packaged for use or filtered under aseptic conditions. and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of modified Factor VII in these formulations can vary widely, i.e., from less than about 0.5%, usually at or at least about 1% to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 10 mg of modified Factor VII. Actual methods for preparing parenterally administrable compounds will be known or apparent to those skilled in the art and are described in more detail in for example, *Remington's Pharmaceutical Science*, 16th ed., Mack Publishing Company, Easton, Pa. (1982), which is incorporated herein by reference.

The compositions containing the modified Factor VII molecules can be administered for prophylactic and/or therapeutic treatments. In therapeutic applications, compositions are administered to a patient already suffering from a disease, as described above, in an amount sufficient to cure or at least partially arrest the disease and its complications. An amount adequate to accomplish this is defined as "therapeutically effective dose." Amounts effective for this use will depend on the severity of the disease or injury and the weight and general state of the patient, but generally range from about 0.05 mg up to about 500 mg of modified Factor VII per day for a 70 kg patient, with dosages of from about 1.0 mg to about 200 mg of modified Factor VII per day being more commonly used. It must be kept in mind that the materials of the present invention may generally be employed in serious disease or injury states, that is, life-threatening or potentially life threatening situations. In such cases, in view of the minimization of extraneous substances and general lack of immunogenicity of modified human Factor VII in humans, it is possible and may be felt desirable by the treating physician to administer substantial excesses of these modified Factor VII compositions.

In prophylactic applications, compositions containing the modified Factor VII are administered to a patient susceptible to or otherwise at risk of a disease state or injury to enhance the patient's own anticoagulative capabilities. Such an amount is defined to be a "prophylactically effective dose." In this use, the precise amounts again depend on the patient's state of health and weight, but generally range from about 0.05 mg to about 500 mg per 70 kilogram patient, more commonly from about 1.0 mg to about 200 mg per 70 kg of body weight.

Single or multiple administrations of the compositions can be carried out with dose levels and pattern being selected by the treating physician. For ambulatory patients requiring daily maintenance levels, the modified Factor VII may be administered by continuous infusion using a portable pump system, for example.

Local delivery of the modified Factor VII may be carried out, for example, by way of perfusion, double balloon catheters, stent, incorporated into vascular grafts or stents, hydrogels used to coat balloon catheters, or other well established methods. In any event, the pharmaceutical formulations should provide a quantity of modified Factor VII of this invention sufficient to effectively treat the patient.

The following examples are offered by way of illustration, not by way of limitation.

EXAMPLE I

Expression of $Ser_{344} \rightarrow Ala_{344}$ Factor VII

To generate the $Ser_{344} \rightarrow Ala$ Factor VII active site mutant, plasmid FVII(565+2463)/pDX (U.S. Pat. No. 4,784,950 incorporated herein by reference; deposited with the American Type Culture Collection under accession number 40205) was digested with Xba I and Kpn I, and the resulting 0.6 kb fragment, comprising the coding region for serine 344, was recovered. This fragment was cloned into Xba I, Kpn I-digested M13mp19 as shown in the Figure. This manipulation and subsequent steps described below were generally performed according to standard protocols (as described, for example, by Maniatis et al., *Molecular Cloning, A Laboratory Manual*, Cold Spring Harbor Laboratory Press, Cold Spring Harbor, N.Y. (1982) incorporated herein by reference).

Mutagenesis was carried out on the M13 template according to the methods of Zoller and Smith, supra, using the mutagenic oligonucleotide ZC1656 (5' TGG GCC TCC GGC GTC CCC CTT 3' SEQ ID NO:3) and the "universal" second primer ZC87 (5' TCC CAG TCA CGA CGT 3' SEQ ID NO:4). Reaction products were screened using kinased ZC1656. Positive plaques were picked, and template DNA was prepared and sequenced from the Pst I site at 1077 to the Kpn I site at 1213. Sequence analysis confirmed the presence of the desired mutation. The mutant clone was designated 1656.

An expression vector was then constructed using the 1656 clone. The mutagenized sequence was isolated from the M13 vector as a ~0.14 kb Pst I-Kpn I fragment. This fragment was ligated to the 1.7 kb Hind III-Xba I fragment from FVII(565+2463)/pDX, the 0.5 kb Xba I-Pst I fragment from FVII(565+2463)/pDX, and the 4.3 kb Kpn I-Hind III fragment from FVII(565+2463)/pDX, as shown in the Figure. The presence of the desired mutant sequence was confirmed by digesting mutant and wild-type clones with Pst I, and a mutant Factor VII insert in M13 with Kpn I and Xba I, preparing Southern blots of the digested DNA, and probing the blots with radiolabeled ZC1656.

The baby hamster kidney cell line BHK 570 (deposited with the American Type Culture Collection under accession number 10314) was transfected with two isolates (designated #544 and #545) of the 1656 expression vector. The cells were prepared by diluting a confluent 10 cm plate of BHK 570 cells 1:10 into five 10 cm plates in non-selective medium (Dulbecco's modified Eagle's medium [DMEM] containing 10% fetal bovine serum and 1% PSN antibiotic mix [GIBCO Life Technologies, Gaithersburg, Md.]). After 24 hours, when the cells had reached 20–30% confluency, they were co-transfected with one isolate of the expression vector encoding the 1656 mutation, plasmid p486 (comprising the Adenovirus 5 ori, SV40 enhancer, Adenovirus 2 major late promotor, Adenovirus 2 tripartite leader, 5' and 3' splice sites, the DHFR$^r$ cDNA and SV40 polyadenylation signal in pML-1 (Lusky and Botchan, *Nature* 293: 79–81, (1981)) and 10 μg of carrier DNA (sonicated salmon sperm DNA) as shown in Table 1. The DNA was added to a 15 ml tube, then 0.5 ml of 2x Hepes (25 g Hepes, 40 g NaCl, 1.8 g KCl, 0.75 g $Na_2HPO_4.2H_2O$, 5 g dextrose diluted to 2.5 l with distilled water and pH adjusted to pH 6.95–7.0) was added and the tubes were mixed. The DNA in each tube was precipitated by the addition of 0.5 ml of 0.25 M $CaCl_2$ while air was bubbled through the DNA/Hepes solution with a pasteur pipet. The tubes were then vortexed, incubated at room temperature for 15 minutes, and vortexed again. The DNA mixtures were then added dropwise onto the plates of cells with a pipette. The plates were swirled and incubated at 37° C. for 4–6 hours. After incubation, 2 ml of 20% glycerol diluted in Tris-saline (0.375 g KCl, 0.71 g $Na_2HPO_4$, 8.1 g NaCl, 3.0 g Tris-HCl, 0.5 g sucrose, diluted in a total of 1 liter and pH adjusted to pH 7.9) was then added to each plate. The plates were swirled and left at room temperature for two minutes. The medium was then removed from the plates and replaced with 2 ml of Tris-saline. The plates were left at room temperature for 2 minutes, then the Tris-saline was removed and replaced with 10 ml of non-selective medium. The plates were incubated at 37° C. for two days.

TABLE 1

| | Transfection* | | | |
|---|---|---|---|---|
| Plasmid Name | 544 | 545 | 544 Control | 545 Control |
| Clone 544 | 15 μl | — | 15 μl | — |
| Clone 545 | — | 30 μl | — | 30 μl |
| p486 | 1.5 μl | 1.5 μl | — | — |
| Carrier DNA | 1.6 μl | 1.6 μl | 1.6 μl | 1.6 μl |

*DNA concentrations used were: clone 544, 0.7 μg/μl; clone 545, 0.3 μg/μl; p486, 1.49 μg/μl.

After the two day incubation, the cells were diluted in selection medium (DMEM containing 10% dialyzed fetal bovine serum, 1% PSN antibiotic mix and 150 nM methotrexate) and 40 plated at dilutions of 1:100, 1:250 and 1;500 in maxi plates.

The plates were incubated at 37° C. for one week. After one week, the medium was changed and replaced with selection medium, and the plates were checked for colony formation.

Eight days later, after colony formation, twelve colonies were randomly chosen from the 1:500 dilution plates of the #544 and #545 transfection plates. Each clone was plated into one well of a 6-well plate and grown in selection medium. After seven days, the plates were confluent, and the clones were each split into 10 cm plates in selection medium.

The clones described above and control cells transfected to express wild-type factor VII were metabolically labeled with $^{35}$S-Methionine-Cysteine Protein Labeling Mix (NEN DuPont Biotechnology Systems, Wilmington, Del.). The clones were grown and prepared for a pulse label experiment in selective medium. The cells were rinsed with phosphate buffered saline (Sigma, St. Louis, Mo.) and pulsed for four hours in 20 μCi/ml $^{35}$S-Cys-$^{35}$S-Met. After four hours, supernatants and cells were harvested. The cells were lysed essentially as described by Lenk and Penman (*Cell* 16: 289–302, (1979)) and 400 μl of each lysate and precleared with 50 pl of staph A (Sigma, St. Louis, Mo.).

Samples from the metabolically labeled cells were radioimmunoprecipitated (RIP) by first incubating the samples with 6 μl of anti-Factor VII polyclonal antisera for four hours. Sixty microliters of washed staphylococcal protein A was added to each sample, and the samples were rocked for 1.5 hours at 40° C. The samples were centrifuged, and the supernatant was removed. The pellets were washed twice in 0.7 M RIPA buffer (10 mM Tris, pH 7.4, 1% deoxycholic acid [Calbiochem Corp., La Jolla, Calif.], 1% Triton X-100, 0.1% SDS, 5 mM EDTA, 0.7 M NaCl) and once in 0.15 M RIPA buffer (10 EM Tris, pH 7.4, 1% deoxycholic acid [Calbiochem Corp., La Jolla, Calif.], 1% Triton X-100, 0.1 SDS, 5 mM EDTA, 0.15 M NaCl). One hundred microliters of 1× SDS dye (50 mM Tris-HCl, pH 6.8, 100 mM dithiothreitol, 2% SDS, 0.1% bromphenol blue, 10% glycerol) was added to each sample, and the samples were boiled for 5 minutes followed by centrifugation to remove the protein A. Fifty microliters of each sample was run on a 10% polyacrylamide gel. Results showed that 9 of 10 clones secreted modified Factor VII.

EXAMPLE II

Anticoagulant Activity of Modified Factor VII

The ability of the modified Factor VII protein to inhibit clotting was measured in a one-stage clotting assay using wild-type Factor VII as a control. Recombinant proteins were prepared essentially as described above from cells cultured in media containing 5μg/ml vitamin K. Varying amounts of the modified Factor VII (from clone 544) or recombinant wild-type Factor VII were diluted in 50 mM Tris pH 7.5, 0.11% BSA to 100 μl. The mixtures were incubated with 100 μl of Factor VII-deficient plasma (George King Bio-Medical Inc., Overland Park, Kans.) and 200 μl of thromboplastin C (Dade, Miami, Fla.; contains rabbit brain thromboplastin and 11.8 mM Ca$^{++}$). The clotting assay was performed in an automatic coagulation timer (MLA Electra 800, Medical Laboratory Automation Inc., Pleasantville, N.Y.), and clotting times were converted to units of Factor VII activity using a standard curve constructed with 1:5 to 1:640 dilutions of normal pooled human plasma (assumed to contain one unit per ml Factor VII activity; prepared by pooling citrated serum from healthy donors). Using this assay the preparations of modified Factor VII exhibited no detectable coagulant activity. Table 2 shows results of the assay in terms of clotting times for control (untransfected) BHX cell-conditioned media (+/− vitamin K), wild-type Factor VII and two isolates of cells expressing the modified Factor VII. Factor VII activity is seen as a reduction in clotting time over control samples.

TABLE 2

| Sample | Dilution | Clotting Time (sec.) |
|---|---|---|
| Control +K | 1:5 | 33.1 |
| | 1:10 | 33.4 |
| Control −K | 1:5 | 34.3 |
| | 1:10 | 33.2 |
| Wild-type | 1:20 | 19.0 |
| Factor VII | 1:40 | 21.5 |
| | 1:80 | 23.3 |
| Modified Factor VII (#6) | 1:1 | 33.5 |
| Modified Factor VII (#10) | 1:1 | 32.5 |

To determine the effect of the modified Factor VII on plasma factor substrates, preparations of modified Factor VII and recombinant wild-type or native Factor VII are incubated with either Factor X or Factor IX and the activation thereof monitored by clotting assays or polyacrylamide gel electrophoresis.

EXAMPLE III

Ability of Modified Factor VII to Bind Tissue Factor

The ability of the modified Factor VII to compete with wild-type Factor VII for tissue factor and inhibit its clotting activity was assessed in a one-step clotting assay in the presence of a limiting amount of tissue factor (thromboplastin).

Clotting times were determined in a one-step assay similar to that described in Example II. A limited amount of tissue factor, a constant amount of wild type Factor VII, and increasing amounts of variant Factor VII were used in the mixing experiments. An inhibition of Factor VII/VIIa procoagulant activity would be seen as an increase in clotting time in assays containing increasing amounts of variant Factor VII.

The amount of Factor VII activity in the test samples was calculated as a percentage of a standard curve that measured Factor VII activity in normal pooled plasma. The standard curve for Factor VII activity was generated using serial dilutions of normal pooled plasma in phosphate buffered solution (PBS) that ranged from 1:5 to 1:640. For this purpose it was assumed that normal plasma contains approximately 500 ng/ml of Factor VII and this was considered to be one unit of activity. A mixture of 100 μl Factor VII-deficient plasma, 100 μl plasma dilution and 200 μl of thromboplastin-C (Dade, Miami, Fla.) was used to measure clotting time on a MLA Electra 800 automatic timer. To establish the standard curve, the results were graphed as percentage of activity (1:5=100% activity) versus clotting time in seconds.

The assay required that the medium containing the wild type and variant Factor VII be composed of less than one percent serum. The dilutions were made in PBS so that clotting times would fall along the standard curve. A minimum dilution of 1:2 was typical. The final volume was 100 μl. Two different human Factor VII $Ser_{344}$→Ala variants, designated clones "#10" and "#6" were tested in the experiments. The results, set forth in the Table below, show that as the amount of Factor VII variant increased, the percent of Factor VIIa activity decreased.

TABLE 3

Results of mixing assay with Ser344 → Ala Variants (B4A1 (wild type) medium was used as 100% activity at 10 μl/reaction)

| Ser344 → Ala Clone No. | Variant medium amount | B4A1 medium amount | BHK Control* | Percent FVIIa Activity |
|---|---|---|---|---|
| #10 | 10 μl | 10 μl | 0 | 70 |
| #10 | 20 μl | 10 μl | 0 | 51 |
| #10 | 30 μl | 10 μl | 0 | 43 |
| #10 | 40 μl | 10 μl | 0 | 34 |
| #10 | 50 μl | 10 μl | 0 | 28 |
| #10 (−K)§ | 20 μl | 10 μl | 0 | 78 |
| #6 | 10 μl | 10 μl | 0 | 74 |
| #6 | 20 μl | 10 μl | 0 | 56 |
| #6 | 30 μl | 10 μl | 0 | 46 |
| #6 | 40 μl | 10 μl | 0 | 41 |
| #6 | 50 μl | 10 μl | 0 | 32 |
| #6 (−K) | 20 μl | 10 μl | 0 | 85 |
| BHK control | 0 | 10 μl | 20 μl | 91 |
| BHK control (−K) | 0 | 10 μl | 20 μl | 107 |

*Untransfected conditioned medium

§For expression of the Factor VII variant, cells were grown in the presence of vitamin K, except where noted "(−K)".

These experiments showed that variants of Factor VII having a $Ser_{344}$→Ala substitution competed with native Factor VII in a dose dependent fashion and inhibited the procoagulant activity of native Factor VII/VIIa. It can thus be concluded that $Ser_{344}$→Ala variant human Factor VII competes with native human Factor VIIa and consequently inhibits activation of Factor X and/or IX in human plasma.

EXAMPLE IV

Reaction of Factor VII with PPACK

Recombinant Factor VII was produced in transfected baby hamster kidney cells. The protein was purified and activated as disclosed by Thim et al. (*Biochemistry* 27: 7785–7793, 1988), Brinkous et al. (*Proc. Natl. Acad. Sci. USA* 86: 1382–1386, 1989) and Bjoern and Thim (*Res. Discl. No.* 269, 564, 1986), which are incorporated herein by reference. The cell culture medium was recovered, filtered and diluted to reduce salt concentration. The diluted medium was then fractionated by anion exchange chromatography using an elution buffer containing $CaCl_2$. The Factor VII fraction was recovered and further purified by immunochromatography using a calcium-dependent anti-Factor VII monoclonal antibody. Additional purification was carried out using two anion exchange chromatography steps wherein Factor VII was eluted using $CaCl_2$ and NaCl, respectively. Factor VIIa was recovered in the final eluate.

Recombinant Factor VIIa (1 $\mu$M) in 50 mM Tris-HCl, 100 mM NaCl, 5 mM CaCl2, ph 7.4 was incubated with 20 $\mu$M PPack (D-Phenylalanyl-Prolyl-Arginyl Chloromethyl Ketone; Calbiochem, La Jolla, Calif.) for 5, 20 and 60 minutes. Buffer containing the chromogenic substrate S2288 (H-D-Isoleucine-L-Prolyl-L-Arginine p-nitroanilide; Kabi Vitrum AB, Molndal, Sweden) was then added to obtain a 2.5 fold dilution and a final concentration of 0.3 mM S2288. The generation of p-nitroaniline was measured and compared to results using untreated Factor VIIa as a control. The results indicated that Factor VIIa is fully inactivated after about 60 minutes under these reaction conditions.

EXAMPLE V

Generation of DEGR-Factor VIIa

Recombinant human Factor VIIa was prepared as described in Example IV. Recombinant human Factor VIIa, in 10 mM glycine buffer, pH 8.0, 10 mM $CaCl_2$, 50 mM NaCl, was diluted to a concentration of 1.5 mg/ml. A 10-fold molar excess of Dansyl-L-Glu-Gly-Arg-Chloromethyl Ketone, DEGRck, (Calbiochem, La Jolla, Calif. 92037) which had been dissolved with distilled $H_2O$ was added to the Factor VIIa. After a 2 hr incubation at 37° C., a second 10-fold molar excess of DEGRck was added to the mixture and incubated for an additional 2 hr at 37° C. A third 10-fold molar excess of DEGRck was added to the Factor VIIa and incubated for approximately 16 hours at 4° C. The DEGR-Factor VIIa sample was then extensively dialyzed at 4° C. against Tris buffered saline (0.05 M Tris-HCl, 0.1 M NaCl, pH 7.5) to remove any free DEGRck.

The final DEGR-Factor VIIa mixture was tested for the presence of free DEGRck in a Factor Xa chromogenic substrate assay. The DEGR-Factor VIIa mixture was added to purified human Factor Xa along with the chromogenic substrate S-2222. This substrate is cleaved specifically by Factor Xa and not by Factor VIIa. Unbound DEGRck in the mixture is able to bind to the Factor Xa and there by inhibit the chromogenic activity of the Factor Xa. Spiking free DEGR-ck into a Factor Xa mixture generated a standard curve to measure the level of free DEGRck in solution versus the inhibition of Factor Xa chromogenic activity. Analysis of the DEGR-Factor VIIa mixture showed that the ratio of free DEGRck:DEGR-Factor VIIa was less than 0.5% following extensive dialysis, thereby ensuring that the inhibition observed by DEGR-Factor VIIa in the various assay systems described below was not due to the presence of free DEGRck.

EXAMPLE VI

Factor Xa Generation on Rat Smooth Muscle Cells

Vascular smooth muscle cells were analyzed for the presence of cell-surface tissue factor by measuring the ability of the cells to stimulate the conversion of Factor X to Factor Xa using a chromogenic substrate that is specific for Factor Xa.

Rat vascular smooth muscle cells (Clowes et al., *J. Clin. Invest.* 93:644–651 (1994)) were plated into 96-well culture dishes (American Scientific Products, Chicago, Ill.) at 8,000 cells per well in growth media (Table 4).

TABLE 4

500 ml Dulbecco's Modified Eagle's Medium (DMEM) (GIBCO-BRL, Gaithersburg, MD.)
10% fetal calf serum (Hyclone, Logan, UT.)
 1 mM sodium pyruvate (Irvine, Santa Ana, CA.)
0.29 mg/ml L-glutamine (Hazelton, Lenexa, KS.)
 1x PSN; (100X is 5 mg/ml penicillin, 5 mg/ml streptomycin, 10 mg/ml neomycin) (GIBCO-BRL, Gaithersburg, MD.)

After a 48 hour incubation at 37° C. the medium was changed to serum free medium (Table 5).

TABLE 5

250 ml Dulbecco's Modified Eagle's Medium (DMEM)
250 ml Ham's F-12 Medium (Fred Hutchinson Cancer Research Center, Seattle, WA)
 1 mM sodium pyruvate
.29 mg/ml L-glutamine
 20 $\mu$M transferrin (JRH, Lenexa, KS.)
  5 $\mu$M insulin (GIBCO-BRL)
 16 ng selenium (Aldrich, Milwaukee, WI.)
  1 mg/ml bovine serum albumin (Sigma, St. Louis, MO)

The cells were incubated 72 hours at 37° C. After incubation, either PDGF-BB (10 ng/ml) or 10% fetal calf serum was added to the cells to stimulate tissue factor expression (Taubman et al., *J. Clin. Invest.* 21:547–552, 1993). A parallel set of cells received neither PDGF nor serum to monitor for intrinsic activity of unstimulated cells. After a 6 hour incubation, recombinant human Factor VIa was added to the cells at a final concentration of 10 nM. One set of cells did not have Factor VIIa added as a negative control. The cells were incubated for 2 hours at 37° C. and washed with HEPES buffer (10 mM HEPES, 137 mM NaCl, 4 mM KCl, 5 mM $CaCl_2$, 11 mM glucose, 0.1% BSA). After washing, cells were incubated for 5 min with 50 $\mu$l per well of 200 nM plasma-purified human Factor X in a Tris-buffered saline supplemented with 5 mM $CaCl_2$. Twenty-five microliters of 0.5 M EDTA and 25 $\mu$l of an 800 $\mu$M solution of S-2222 chromogenic substrate (Kabi Pharmacia, Franklin, Ohio.) were added to each well. The plates were incubated for 40 min at room temperature, then analyzed at 405 nm using a THERMOMAX microplate reader (Molecular Devices, Menlo Park, Calif.).

Table 6 shows an increase in absorbance for the Factor VIIa treated wells as compared to the control wells (no Factor VIIa added). The increase in absorbance is a direct measurement of the level of Factor Xa generated in the wells and its subsequent cleavage of the chromogenic substrate, releasing the chromophore. The data also demonstrate that the level of chromogenic activity in cells pretreated with either PDGF-BB or 10% fetal calf serum was higher than unstimulated cells.

TABLE 6

| Test Sample | OD$_{405}$ |
| --- | --- |
| Control | .043 |
| Intrinsic | .247 |
| PDGF-BB | .360 |
| 10% FCS | .342 |

These results clearly show there is a Factor VIIa-dependent activation of Factor X to Factor Xa on the cell surface of rat vascular smooth muscle cells.

EXAMPLE VII

Inhibition of Cell-Surface Chromogenic Activity By DEGR-Factor VIIa

Rat vascular smooth muscle cells were plated into 96-well culture dishes as described above. The cells were cultured for 72 hours in serum free media as described above and treated with the addition of 10% fetal calf serum for 6 hours to stimulate tissue factor expression. After stimulation, buffer only (control), 10 nM Factor VIIa, or 10 nM Factor VIIa+100 nM DEGR-Factor VIIa was added to each well. The cells were incubated for 2 hours at 37° C., then washed with HEPES buffer. After washing, the cells were incubated for 5 minutes with 50 µl per well of 200 nM Factor X in Tris-buffered saline supplemented with 5 mM CaCl$_2$. Twenty-five microliters of 0.5 M EDTA and 25 µl of S-2222 (800 µM) chromogenic substrate (Kabi Pharmacia) were added to each well. The cells were incubated at room temperature for 40 minutes. Chromogenic activity was analyzed at 405 nm as described above.

Table 7 shows stimulation of chromogenic activity in the wells treated with Factor VIIa only, and inhibition of stimulation when DEGR-Factor VIIa was co-incubated with the Factor VIIa. These results demonstrate that DEGR-Factor VIIa acts as a competitive antagonist for Factor VIIa binding, thereby inhibiting the activation of Factor X to Factor Xa and the subsequent cleavage of the S-2222 chromogen.

TABLE 7

| Test Sample | OD$_{405}$ |
| --- | --- |
| Control | .035 |
| Factor VIIa | .342 |
| Factor VIIa + DEGR-Factor VIIa | .073 |

EXAMPLE VIII

Dose Dependent Inhibition by DEGR-Factor VIIa of Cell Surface Chromogenic Activity on Rat Smooth Muscle Cells Rat vascular smooth muscle cells were plated into 96-well culture dishes at 4,000 cells per well in growth medium supplemented with 1% fetal calf serum (as in Table 4 without 10% fetal calf serum). After 5 days the medium was removed, and either increasing concentrations of Factor VIIa alone or 10 nM Factor VIIa with increasing concentrations of DEGR-Factor VIIa were added to the cells. The cells were incubated with the Factor VII mixtures for 2 hours at 37° C. After incubation, the cells were washed and incubated with 50 µl of 200 nM Factor X in tris buffered saline for 5 minutes at room temperature. Each well had 25 µl of 0.5 M EDTA and 25 µl of 800 µM S-2222 (Kabi Pharmacia) added to it, and the plates were incubated for 40 minutes at room temperature. Chromogenic activity was analyzed at 405 nm in a microplate reader as described above.

Table 8 shows a dose-dependent increase in chromogenic activity with increasing amounts of Factor VIIa added to the wells. When the mixture of DEGR-Factor VIIa with 100 nM Factor VIIa was added to the cells (Table 9) there was a dose dependent inhibition in chromogenic activity. A 1:1 molar ratio of DEGR-Factor VIIa:Factor VIIa inhibited approximately 95% of the chromogenic activity. These data suggest that in this experimental design DEGR-Factor VIIa has a significantly higher affinity for cell-surface tissue factor than native Factor VIIa on smooth muscle cells in culture. If DEGR-Factor VIIa and Factor VIIa had equal affinity for binding tissue factor then the level of inhibition observed when the two molecules were added to the cells in an equal molar ratio would not have been as high.

TABLE 8

| Factor VIIa Conc. (nM) | OD$_{405}$ |
| --- | --- |
| .10 | .005 |
| .39 | .025 |
| 1.56 | .058 |
| 6.25 | .111 |
| 25.00 | .154 |
| 100.00 | .208 |

Table 9 shows the dose dependent inhibition of Factor Xa chromogenic activity on rat smooth muscle cells by DEGR-Factor VIIa. Increasing concentrations of DEGR-Factor VIIa were co-incubated with 100 nM Factor VIIa, and the Factor Xa chromogenic activity determined using chromogenic substrate S-2222.

TABLE 9

| DEGR-Factor VIIa Conc. (nM) | OD$_{405}$ |
| --- | --- |
| .00 | .208 |
| .39 | .176 |
| 1.56 | .116 |
| 6.25 | .073 |
| 25.00 | .026 |
| 100.00 | .014 |

EXAMPLE IX

Inhibition of Factor Xa generation by DEGR-Factor VIIa in a soluble tissue factor assay.

The conversion of Factor X to Factor Xa using purified recombinant soluble tissue factor was established using a chromogenic assay. Tissue factor was expressed and purified from *Saccharomyces cerevisiae* (Shigematsu et al., *J. Biol. Chem.* 267:21329–21337, 1992). Soluble tissue factor was purified and characterized by Dr. W. Kisiel (University of New Mexico). A reaction mixture containing 65.9 µl of soluble tissue factor (2.2 µM), 29.0 µl of PCPS (1 mM, Sigma, St. Louis, Mo.), 29.5 µl human Factor X (4.1 µM), 2.77 ml Hank's buffer (25 mM Tris, pH 7.4, 150 mM NaCl, 2.7 mM KCl, 5 ]nM CaCl$_2$, 0.1% BSA) was prepared. Forty microliter of tissue factor/Factor X mixture, 25 µl Factor VIIa diluted with TBS and 25 µl of DEGR-Factor VIIa diluted with TBS were added to each well of a 96-well microtiter plate. A control using 40 pl of tissue factor/Factor X mixture; 25 μl Factor VIIa diluted with TBS, and 25 μl of TBS only was included. Ten microliters of S-2222 (4 mM) chromogenic substrate was added to the reaction mixture in the wells and incubated at room temperature for 2–10 minutes. Results were analyzed at 405 nm in a microplate reader as described above.

Determination of a standard curve for Factor VIIa activation of Factor X was made using increasing concentrations of Factor VIIa added in the absence of DEGR-Factor VIIa. The results, presented in Table 10, show that there is a dose-dependent increase in chromogenic activity with increasing amounts of Factor VIIa added to the reaction mixture. The simultaneous addition of varying amounts of DEGR-Factor VIIa and 100 nM Factor VIIa led to a dose dependent decrease in chromogenic activity (Table 11). These data demonstrate that DEGR-Factor VIIa acts as a competitive antagonist for native Factor VIIa binding to soluble tissue factor, and thereby inhibits the generation of Factor Xa as measured by the decrease in chromogenic activity towards the chromogenic substrate S-2222.

TABLE 10

Stimulation of Factor Xa chromogenic activity with increasing concentrations of Factor VIIa added to soluble tissue factor. Changes in optical density were measured using chromogenic substrate S-2222.

| Factor VIIa Conc (nM) | $OD_{405}$ |
|---|---|
| .78 | .168 |
| 1.56 | .288 |
| 3.12 | .478 |
| 6.25 | .694 |
| 12.50 | .764 |
| 25.00 | .790 |
| 50.00 | .738 |
| 100.00 | .770 |

TABLE 11

Inhibition of Factor Xa chromogenic activity by the addition of DEGR-Factor VIIa to soluble tissue factor in the presence of native Factor VIIa is measured. Changes in optical density were measured using the chromogenic substrate S-2222.

| DEGR-Factor VIIa Conc. (nM) | $OD_{405}$ |
|---|---|
| 0 | .810 |
| 50 | .750 |
| 100 | .609 |
| 200 | .296 |
| 400 | .167 |
| 800 | .083 |
| 1600 | .055 |

EXAMPLE X

Inhibition of Coagulation by DEGR-Factor VIIa

Standard clotting assays to monitor the effect of DEGR-Factor VIIa on clotting time were prepared as follows: 100 μl of normal baboon plasma, collected with sodium citrate as anticoagulant, was added to 100 μl of varying concentrations of DEGR-Factor VIIa diluted in TBS (20 mM Tris, pH 7.4, 150 mM NaCl). The samples were mixed and briefly incubated at 37° C. The samples were added to an Electra 800 Automatic Coagulation Timer (Medical Laboratories Automation, Pleasantville, N.Y.). After incubation, 200 μl of a tissue factor preparation containing 25 mM $CaCl_2$ was added to the DEGR-Factor VIIa preparations. A tissue factor preparation was made as a saline extract of baboon brain from freshly frozen brain tissue and characterized for its ability to initiate coagulation in baboon plasma. A concentration of tissue factor that gave a clotting time of about 40 seconds was selected.

The data, presinted in Table 12, demonstrates a dose-dependent increase in clotting time due to the addition of DEGR-Factor VIIa. A dose as low as 1 μg/ml of DEGR-Factor VIIa in plasma resulted in a significant increase in clotting time.

TABLE 12

Dose dependent increase in clotting time due to DEGR-Factor VIIa.

| DEGR-Factor VIIa (μg/ml plasma) | Clotting time (seconds) |
|---|---|
| 0 | 40.7 |
| 0.5 | 46.2 |
| 1.0 | 50.8 |
| 2.5 | 64.5 |
| 5.0 | 108.1 |
| 10.0 | 158.4 |

EXAMPLE XI

Inhibition of Platelet Accumulation With DEGR-Factor VIIa

DEGR-Factor VIIa was analyzed for its ability to inhibit platelet accumulation at sites of arterial thrombosis due to mechanical injury in non-human primates. A model of aortic endarterectomy was utilized in baboons, essentially as described by Lumsden et al. (*Blood* 81:1762–1770 (1993)). A section of baboon aorta 1–2 cm in length was removed, inverted and scraped to remove the intima of the artery and approximately 50% of the media. The artery was reverted back to its correct orientation, cannulated on both ends and placed into an extracorporeal shunt in a baboon, thereby exposing the mechanically injured artery to baboon blood via the shunt. Just prior to opening of the shunt to the circulating blood, $^{111}$In-labeled autologous platelets were injected intravenously into the animal. The level of platelet accumulation at the site of the injured artery was determined by real-time gamma camera imaging.

Figure 2:
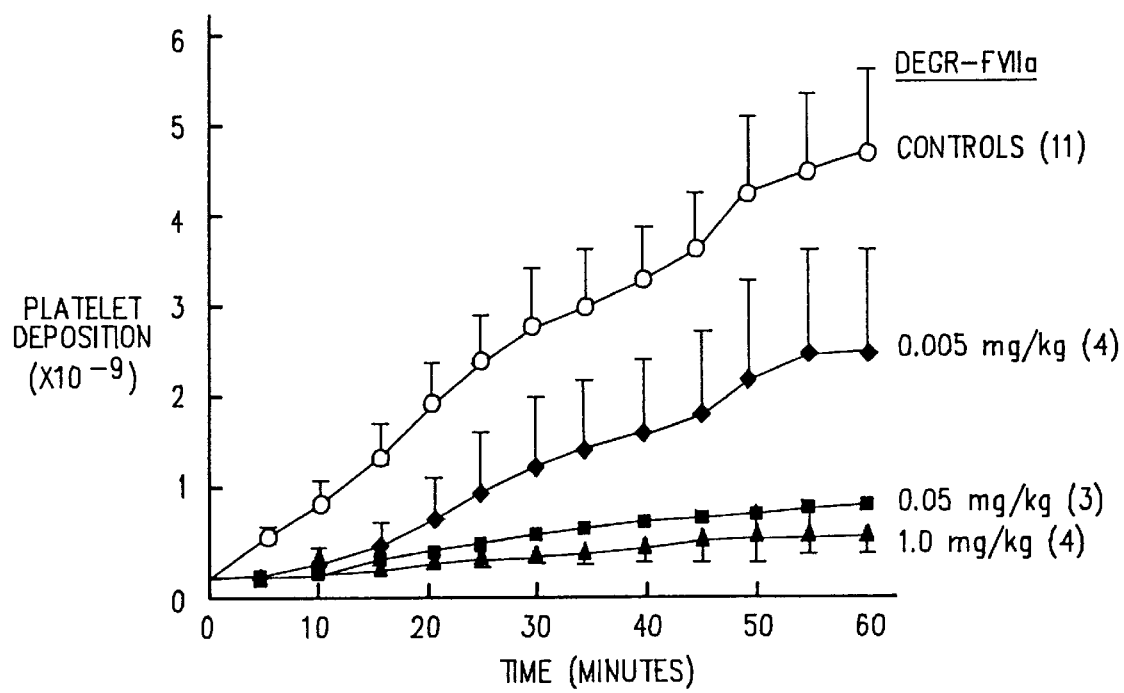
FIG. 2 shows the effect of bolus injection of DEGR-Factor VIIa on thrombus formation (platelet deposition) on endarterectomized baboon aorta when compared to saline-treated controls. The arteries were measured over 60 minutes. The DEGR-Factor VIIa significantly inhibited the development of platelet-rich thrombi in this primate model of acute vascular injury.

Evaluation of DEGR-Factor VIIa for inhibition of platelet accumulation was done using bolus injections of DEGR-Factor VIIa or saline control and were given just prior to the opening of the shunt. The injured arteries were measured continuously for 60 minutes. A dose of 0.005 mg/kg of DEGR-Factor VIIa inhibited platelet accumulation. At a 1.0 mg/kg bolus injection, approximately 90% of platelet accumulation was inhibited at 1 hour post drug administration. These results are shown in FIG. 2.

These data show that inhibition of tissue factor with DEGR-Factor VIIa can significantly inhibit the development of platelet-rich thrombi in a nonhuman primate model of acute vascular injury.

EXAMPLE XII

DEGR-FVIIa Inhibits Vascular Restenosis Following Balloon Angioplasty in Atherosclerotic Rabbits DEGR-FVIIa was evaluated for its ability to modulate lesion development following balloon angioplasty in New Zealand White (NZW) atherosclerotic rabbits. This animal model has been well characterized and has proven to be a good model for evaluating anti-thrombotic compounds on vascular lesion development (Gimple et al., *Circulation* 86:1536–1546 (1992), and Rogosta et al., *Circulation* 89:1262–1271 (1994)). The animal model used to evaluate DEGR-FVIIa is essentially as described by Ragosta, ibid.

Anesthesia was induced in rabbits with 5 mg/kg xylazine and 35 mg/kg ketamine by intramuscular injection. The proximal femoral arteries were exposed by cutdown below the inguinal ligament with proximal and distal ligatures. The isolated segments were cannulated with 27 gauge needles. A vent was created by needle puncture. The isolated segments were flushed with saline to clear residual blood, and desiccated by air infused at a rate of 80 ml/min for 8 minutes. Following air-drying, the isolated segments were again flushed with saline and the ligatures removed. Hemostasis was maintained with non-occlusive local pressure. The segments were demarcated with metal clips. Local spasm was treated with Xylocaine 1% locally. The day following surgery, the animals were placed on 1% cholesterol and 6% peanut oil diet for one month until balloon angioplasty. Tylenol 10 mg/kg orally was given for postoperative pain relief for 3–5 days. Ambipen 1cc was given after the surgical procedure during postoperative days 3 to 5.

The test drug delivery for the animals consisted of an initial bolus injection immediately prior to balloon angioplasty, followed by a continuous systemic infusion by osmotic pump via the internal jugular vein. The duration of the drug infusion was 3 days. The control animals received heparin, 150 U/kg IV bolus, prior to balloon angioplasty followed by saline infusion. The DEGR-FVIIa treated animals received a 1 mg/kg bolus injection followed by 50 µg/kg/hr infusion.

For the placement of the osmotic pumps for continuous systemic infusion, anesthesia was induced in the animals as described above, and maintained throughout the procedure with additional IM injections of ketamine and Xylazine. Through a midline neck incision, the right internal jugular vein was isolated by blunt dissection and the distal end ligated. A silastic tube (PE-160) was introduced into the right internal Jugular vein. A subcutaneous tunnel was created to pass the silastic tube. This tube was connected with the osmotic pump. The osmotic pump was implanted subcutaneously in the back of the rabbit. The right common carotid artery was isolated by blunt dissection and the distal end ligated. Via an arteriotomy, a 5F introducer was placed and advanced to the junction of the aortic arch. Blood was drawn for determination of hemostatic parameters, drugs and cholesterol levels. Twenty milligrams of xylocain was injected intraarterially. A control aortoiliofemoral angiogram was performed via a 5F Berman catheter positioned above the aortic bifurcation using 3–4 ml renographin injected over 3 seconds by hand.

After removal of the Berman catheter, a 0.014-inch guidewire was introduced in the descending aorta and positioned above the aortic bifurcation. Under fluoroscopic guidance, an appropriately sized balloon angioplasty catheter of 2.0 to 2.5 mm was introduced and advanced over the guidewire and positioned across the stenosis. The balloon was inflated to 6 atmospheres for 60 seconds with a hand inflator. Three inflations were performed with 60 second intervals between inflations. This procedure was performed in both femoral arteries in each animal.

Following balloon dilatation, the angioplasty catheter was withdrawn and the Berman catheter reintroduced to a position 3 cm above the aortic bifurcation. To minimize spasm 20 mg of lidocaine was given intraarterially. A post procedure angiogram was performed as described above. A 1 cm grid was positioned at the level of the femoral artery to calculate the actual diameter. The catheter was then removed. The right carotid artery was ligated with 3–0 silk and the wound sutured by layers. Ambipen and acetaminophen were given as above.

Prothrombin time and concentration of DEGR-FVIIa in the blood were determined at immediately pre-bolus injection of the test compound, 1 hr post bolus injection, and at 3 days at the end of continuous infusion. One to two mls of citrated plasma was obtained and the prothrombin times and antigen levels determined.

A standard clotting assay was used to monitor the prothrombin time in the control and DEGR-FVIIa-treated animals as follows. Twenty-five microliters of test rabbit plasma, collected with sodium citrate as anticoagulant, was added to 150 µl of TBS (20 mM Tris, pH 7.4, 150 mM NaCl). The samples were mixed and added to an Electra 800 Automated Coagulation Timer (Medical Laboratories Automation, Pleasantville, N.Y.). After incubation, 200 µl of thromboplastin preparation (Sigma Chemical) containing 25 mM $CaCl_2$ was added to the plasma preparations. A concentration of thromboplastin that gave a clotting time of approximately 20 seconds in the control rabbit plasma was selected.

An ELISA assay was used to determine the concentration of DEGR-FVIIa in plasma samples from the control and DEGR-FVIIa treated rabbits. The assay involved first diluting an anti-human FVII monoclonal antibody (Dr. W. Kisiel, U. of New Mexico) to 2.0 µg/ml in 0.1 M carbonate buffer pH 9.6, and adding 100 µl/well to 96-well plates. The plates were then incubated at 4° C. overnight and subsequently washed two times using wash buffer (PBS, pH 7.4, containing 0.05% Tween 20). Blocking of nonspecific binding sites was achieved with 200 µl of blocking buffer per well (PBS, pH 7.4, containing 0.05% Tween 20 and 1% BSA) incubated at 37° C. for 2 hr, followed by a wash using the wash buffer.

After blocking, a standard dilution series of DEGR-FVIIa ranging from 20–0.027 ng/ml was added, along with a dilution series of the test rabbit plasma (1:100 to 1:4000 in blocking buffer) applied at 100 µl/well. Non-immune rabbit plasma was used as a negative control. Plates were then incubated for 1 hr at 37° C. followed by four washes with wash buffer.

DEGR-FVIIa was detected by adding 100 µl/well of a 1:1,000 dilution of rabbit anti-human FVII polyclonal antibody (Dr. Kisiel, U. New Mexico) in blocking buffer. Plates were incubated for 1 hr at 37° C., followed by five washes with wash buffer. Specific antibody binding was detected using 100 µl/well of a 1:2,000 dilution of goat anti-rabbit IgG antibody-peroxidase conjugate (Tago, Inc.). Plates were incubated for 1 hr at 37° C. and washed six times with wash buffer. Finally, 100 µl of substrate solution was added (0.42 mg/ml of o-phenylenediamine dihydrochloride [OPD] in 0.2 M citrate buffer, pH 5.0, containing 0.3% $H_2O_2$). After 1–3 min at room temp. the color reaction was stopped by adding 100 µl/well of 1N $H_2SO_4$ and the plates were read at 490 nm on a Microplate spectrophotometer. The concentration of DEGR-FVIIa in the plasma samples was determined by comparing the $A_{490}$ values of the unknown to those of the DEGR-FVIIa standard curve.

Analysis of plasma samples for prothrombin times and DEGR-FVIIa antigen levels is shown in Table 13 and Table 14, respectively. The data are presented for each individual animal. Table 15 shows a summary of the mean clotting times. In all cases, the DEGR-FVIIa treated animals had elevated prothrombin times at the 1 hr post-bolus injection time point which returned to near pre-treatment levels at the 3-day time point. Analysis of the DEGR-FVIIa antigen levels also showed a high level of DEGR-FVIIa in the plasma at the 1 hr time point, ranging between 2–6 μg/ml in the plasma, with much lower circulating levels at the 3 day time point. The levels of DEGR-FVIIa measured at the 1 hr time period correspond with a predicted increase in prothrombin time, as determined by spiking normal rabbit plasma with DEGR-FVIIa in vitro and determining prothrombin times in a standard dilute thromboplastin assay.

TABLE 13

MEASUREMENT OF PROTHROMBIN TIMES

| Animal | | Clotting Time (seconds) | | |
| --- | --- | --- | --- | --- |
| Number | Treatment | Pretreatment | 1 hour | 3 days |
| 73 | Control | 24.8 | 22.3 | 17.8 |
| 74 | Control | 24.8 | 27.9 | 18.6 |
| 75 | Control | 24.6 | N/D | 20.5 |
| 76 | Control | 22 | N/D | 17.9 |
| 169 | Control | 21.2 | 22.9 | 22 |
| 170 | Control | 24.9 | 23.5 | 18.6 |
| 173 | Control | 25.9 | 21 | 20.8 |
| 174 | Control | 25 | 29.4 | 20.1 |
| 77 | DEGR-FVIIa | 22.5 | 40.1 | 18.3 |
| 78 | DEGR-FVIIa | 24.3 | 34 | 20.9 |
| 80 | DEGR-FVIIa | 24.7 | 50 | 21.7 |
| 96 | DEGR-FVIIa | N/A | N/A | 21 |
| 97 | DEGR-FVIIa | 23.6 | 33.3 | 21.2 |
| 171 | DEGR-FVIIa | 20.6 | 45.8 | 21.9 |
| 172 | DEGR-FVIIa | 23.5 | 41.6 | 22.4 |

N/A - Data Not Available

TABLE 14

ELISA TO DETECT DEGR-FVIIa IN RABBIT PLASMA

| | | FVIIa ELISA (ng/ml) | | |
| --- | --- | --- | --- | --- |
| Animal Number | Treatment | Pretreatment | 1 hour | 3 days |
| 73 | Control | 0 | 13 | 0 |
| 74 | Control | 36 | 14 | 4 |
| 75 | Control | 0 | N/A | 9 |
| 76 | Control | 0 | N/A | 14 |
| 169 | Control | 0 | 0 | 1 |
| 170 | Control | 0 | 0 | 0 |
| 173 | Control | 36 | 31 | 0 |
| 174 | Control | 87 | 86 | 160 |
| 77 | DEGR-FVIIa | 0 | 3,210 | 102 |
| 78 | DEGR-FVIIa | 1 | 4,950 | 7 |
| 80 | DEGR-FVIIa | 13 | 4,543 | 661 |
| 96 | DEGR-FVIIa | 65 | 4,900 | 117 |
| 97 | DEGR-FVIIa | 4 | 4,600 | 502 |
| 171 | DEGR-FVIIa | 13 | 2,145 | 212 |
| 172 | DEGR-FVIIa | 9 | 2,830 | 228 |

N/A = Data Not Available

TABLE 15

Statistical Summary of Plasma Clotting Times.

| Unpaired t-Test X | | PRE-BLEED | | |
| --- | --- | --- | --- | --- |
| DF: 12 | Unpaired t Value: 1.12 | | Prob. (2-tail): .2852 | |
| Group: | Count: | Mean: | Std. Dev.: | Std. Error |
| Control | 8 | 24.15 | 1.64 | .58 |
| DEGR-VIIa | 6 | 23.2 | 1.48 | .6 |

TABLE 15-continued

Statistical Summary of Plasma Clotting Times.

| Unpaired t-Test X | | 1 Hr POST ANGIO | | |
| --- | --- | --- | --- | --- |
| DF: 10 | Unpaired t Value: −5.44 | | Prob. (2-tail): .0003 | |
| Group: | Count: | Mean: | Std. Dev.: | Std. Error |
| Control | 6 | 24.5 | 3.35 | 1.37 |
| DEGR-VIIa | 6 | 40.8 | 6.53 | 2.67 |

| Unpaired t-Test X | 3 Days POST ANGIO | | | |
| --- | --- | --- | --- | --- |
| DF: 13 | Prob. (2-tail): .0622 | | | |
| Unpaired t Value: −2.04 | | | | |
| Group | Count | Mean | Std. Dev. | Std. Error |
| Control | 8 | 19.54 | 1.53 | .54 |
| DEGR-VIIa | 7 | 21.06 | 1.33 | .5 |

Three weeks post-angioplasty a follow-up angiogram was repeated as described above via the left carotid artery immediately prior to sacrifice. Through a vertical lower abdominal incision, the distal aorta was isolated, tied off proximally, and the perfusion cannula inserted above the aortic bifurcation. The distal aorta was flushed with 50 ml of saline followed by in vivo fixation with 500 ml of Histochoice (AMRESCO, Solon, Ohio.) solution infused over 15 mins at 120 mmHg. Once perfusion was started, the animals were sacrificed with an overdose of nembutal (3 ml sodium pentobarbital IV, 65 mg/ml). A 5 cm segment of femoral artery was excised bilaterally. The tissue was preserved in Histochoice solution for light microscopy.

To determine intimal lesion development at the site of balloon angioplasty, the excised femoral arteries were cut in serial 3 mm sections, embedded in paraffin, and sections cut from multiple regions of each artery. The sections were mounted onto glass slides and the slides stained with hematoxylin and eosin, and Van Giemson stains. Morphometric analysis was performed with Bioquant Program to obtain area measurements for the lumen, the intima and the media. Morphometric analysis of tissue sections from the injured arteries were done measuring the total luminal area; the area of the intima, determined by measuring the area within the internal elastic lamina and subtracting the corresponding luminal area from each tissue section; and the area of the media, determined by measuring the area inside the external elastic lamina and subtracting the area inside the internal elastic lamina. Measurements for intimal lesions in the femoral arteries in control and DEGR-FVIIa treated animals showed that there was a significant decrease in the size of the intima in the DEGR-FVIIa treated animals (Table 16). In contrast, measurement of the medial area showed no significant difference between the two groups.

TABLE 16

MEASUREMENTS OF THE INTIMA AND MEDIA IN BALLOON ANGIOPLASTY TREATED RABBITS

| Group | N | | Std. Dev. | Prob. (2-tail) |
| --- | --- | --- | --- | --- |
| | | Intima (mm2) | | |
| Control | 13 | 0.819 | 0.414 | 0.0138 |
| DEGR-FVIIa | 10 | 0.438 | 0.192 | |
| | | Media (mm2) | | |
| Control | 13 | 0.389 | 0.098 | 0.172 |
| DEGR-FVIIa | 10 | 0.329 | 0.105 | |

The data from the angiographic measurements are presented in Table 17 as the Mean Luminal Diameter (MLD)

+/−standard deviation for the control and DEGR-FVIIa treated animal for all three time points: immediately pre-angioplasty, immediately post-angioplasty, and 21 days post-angioplasty. There was no significant difference in the MLD between the control and DEGR-FVIIa treated animals at either the pre- or immediately post-angioplasty measurements. A significant increase in MLD was observed, however, in the DEGR-FVIIa treated animals at the 21 day post-angioplasty measurement.

TABLE 17

MEASUREMENT OF MINIMAL LUMINAL DIAMETER (MLD)

| Group | N | Meal MLD | Std. Dev. | Prob. (2-tail) |
|---|---|---|---|---|
| Pre-PTCA Measurement of MLD | | | | |
| Control | 13 | 1.202 | 0.24 | 0.3883 |
| DEGR-FVIIa | 10 | 1.283 | 0.19 | |
| Post-PTCA Measurement of MLD | | | | |
| Control | 13 | 1.492 | 0.551 | 0.5326 |
| DEGR-FVIIa | 10 | 1.323 | 0.725 | |
| 21 Day Measurement of MLD | | | | |
| Control | 13 | 0.889 | 0.228 | 0.0001 |
| DEGR-FVIIa | 10 | 1.393 | 0.242 | |

EXAMPLE XIII

Inhibition of Cell-Surface Factor Xa Generation on Baboon SMCs by DEGR-FVIIa

A cell-surface chromogenic assay was developed, essentially as described in Example VIII above, to measure the efficacy of DEGR-FVIIa to block FVIIa binding to cell-surface tissue factor and the subsequent conversion of Factor X to Factor Xa on monolayers of baboon smooth muscle cells (SMCs). This method is a modification of those described by Sakai et al., *J. Bio. Chem.* 264:9980–9988 (1989) and Wildgoose et al., *Proc. Natl. Acad. Sci. USA.* 87:7290–7294 (1990). Baboon SMCs were obtained from the University of Washington, Seattle, Wash., and were cultured from aortic explants. The baboon SMCs were plated into 96-well culture dishes at a concentration of 8,000 cells/well in 200 μl/well DMEM culture media supplemented with 10% fetal calf serum, and maintained in this media for 4 days at 37° C. in 5% $CO_2$. At the time of assay 110 μl of culture media was removed, and increasing concentrations of FVIIa or FVIIa in combination with DEGR-FVIIa were added to wells. A standard curve for FVIIa concentration was generated, ranging from 5 nM to 0.04 nM. To measure the inhibitory activity of DEGR-FVIIa on FVIIa activity, increasing concentrations of DEGR-FVIIa were added to test wells in the presence of a constant amount of FVIIa (5 nM). Both FVIIa and DEGR-FVIIa were diluted with HEPES buffer (10 mM HEPES, 137 mM NaCl, 4 mM KCl, 5 mM $CaCl_2$, 11 mM glucose, 0.1% BSA) and 10 μl of 10× stock solutions added to the cells. The cells were incubated with the test compounds for 2 hr at 37° C., then washed 3 times with HEPES buffer. Fifty microliters of a 200 nM solution of Factor X in Tris buffer (25 mM Tris, pH 7.4, 150 mM NaCl, 2.7 mM KCl, 5 mM $CaCl_2$, 0.1 BSA) was then added to each well. After 4 mins at room temp., 25 μl of 0.5 M EDTA was added to stop the Factor X to Xa conversion. Twenty-five microliters per well of 0.8 mM S-2222, a factor Xa-specific chromogenic substrate, in Tris buffer was added and the absorbance at 405 nM read after 60 mins in a Thermomax microplate reader (Molecular Devices Corp., Menlo Park, Calif.).

Figure 3:
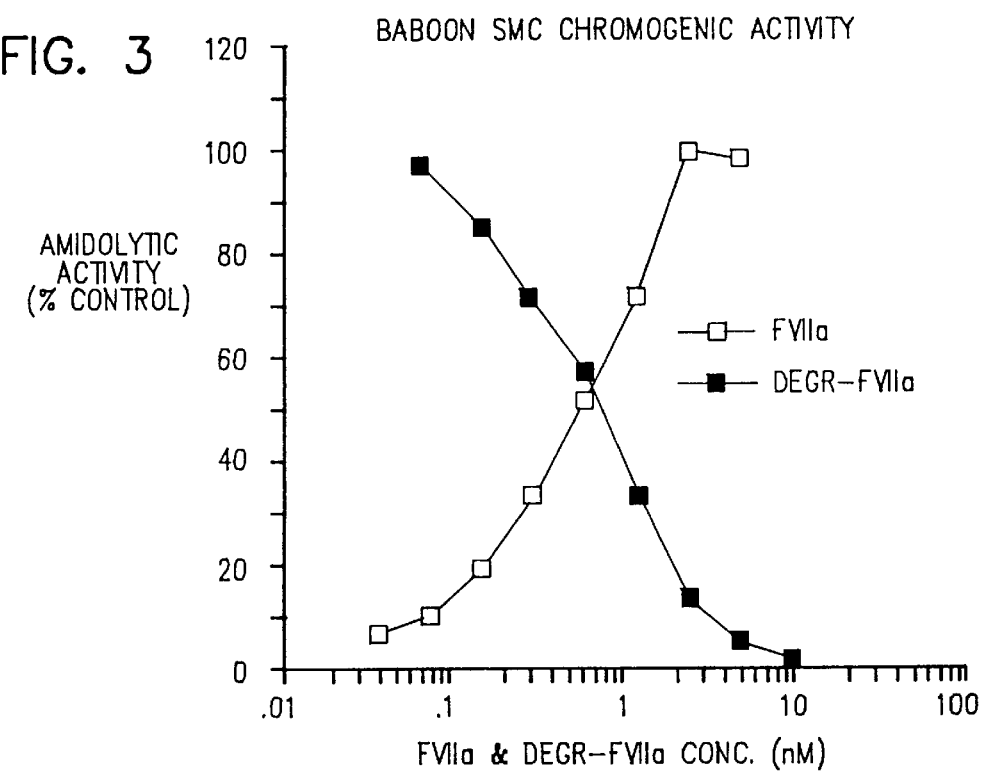
FIG. 3 shows results obtained when baboon smooth muscle cells were incubated with increasing concentrations of either FVIIa (open box), or DEGR-FVIIa in the presence of a constant amount of FVIIa (5 nM) (closed box). The level of FX activation was subsequently determined using the chromogenic substrate S-2222. The data are presented as the amidolytic activity as a percentage of the activity generated in the presence of 5 nM FVIIa alone.

The results, shown in FIG. 3, demonstrate a dose dependent increase in amidolytic activity for the FVIIa treated wells (open boxes). The increase in absorbance is a direct measure of the level of Factor Xa generated in the wells and its subsequent cleavage of the chromogenic substrate. The addition of increasing amounts of DEGR-FVIIa with a constant amount of FVIIa (5 nM) showed a dose dependent decrease in amidolytic activity with increasing levels of DEGR-FVIIa (closed boxes). An equal molar ratio of DEGR-FVIIa to FVIIa was able to inhibit >90% of the chromogenic activity. Even at a 10-fold lower level of DECR-FVIIa, there was still a 40% inhibition in the generation of Factor Xa chromogenic activity. These results support the conclusion that DEGR-FVIIa is an extremely potent antagonist of the activation of Factor X to Xa by FVIIa on the surface of intact cell monolayers of SMCs.

EXAMPLE XIV

Effect of DEGR-Factor VIIa on Vascular Thrombosis Formation and Vascular Lesion Formation in Baboons Human DEGR-Factor VIIa was tested for the ability to inhibit tissue factor (TF) and activated Factor VII (FVIIa) mediation of vascular lesion formation (VLF) induced by mechanical vascular injury in nonhuman primates.

Beginning immediately prior to creating mechanical vascular injury in baboons, DEGR-Factor VIIa was infused intravenously for 7 days (5 animals) or 30 days (1 animal). Measurements were performed for vascular lesion formation on day 30. The results in 5 treated animals were compared with the findings in 5 concurrent vehicle buffer-infused controls.

Baseline measurements were obtained on study animals for: a) platelet counts, neutrophil counts, monocyte counts and red cell counts; b) plasma fibrinogen level; c) activity levels of plasma coagulation factors VII, VIIa, X and V, together with the antigenic levels of FVII; and d) baseline plasma sample for anti-Factor VIIa antibody level.

Under halothane anesthesia and sterile operating conditions, animals labeled with autologous $^{111}$In-platelets received intravenous infusions of DEGR-FVIIa using the tether system for continuous intravenous administration (initial bolus injection of 1 mg/kg followed by continuous intravenous infusion of 50 μg/kg/hr. The animals received surgical carotid endarterectomy, bilateral brachial artery or bilateral femoral artery Fogarty balloon catheter angioplasties.

The DEGR-FVIIa was administered for 7 or 30 days by continuous infusions via venous catheter using the tether system. Thirty days after surgery the animals were anesthetized with halothane and underwent in situ pressure-perfusion fixation with 4% paraformaldehyde containing 0.1% glutaraldeyde for 30 min. At that time, vascular segments (containing the sites previously injured) were harvested using procedures of Harker et al., *Circulation* 83:41–44 (1991) and Hanson et al., *Hypertension* 18:I1170-I176 (1991). The specimens were post-fixed in vitro (4% paraformaldehyde containing 0.1% glutaraldehyde), cryo-preserved and processed for morphometric analysis of lesion extent.

Eleven normal mature baboons (Paio anubis) were studied. Six animals received DEGR-FVIIa infusions (50 μg/kg/hr) and the remaining five were control animals that did not receive DEGR-FVIIa. The animals were dewormed and observed to be disease-free for three months prior to use. All procedures were approved by the Institutional Animal Care and Use Committee and were in compliance with procedures and methods outlined by NIH Guide for the Care and Use of Laboratory Animals, as well as the Animal Welfare Act and related institutional policies. Invasive procedures were carried out under halothane anesthesia after induction by ketamine (10 mg/kg intramuscularly) and valium (0.5 mg/kg intravenously). For subsequent short-term immobilization in performing experimental procedures postoperatively, ketamine hydrochloride (5–20 mg/kg intramuscularly) was used.

Carotid endarterectomy was performed through a midline neck incision using the technique of Hanson et al., *Hypertension* 18:1170-I-176 (1991) and Krupski et al., *Circulation* 84:1749–1757 (1991), incorporated herein by reference. Endarterectomy was used as a vascular injury model because of its clinical relevance, and because VLF induced by endarterectomy of normal arteries has been shown to be reproducible. In brief, the common carotid artery was dissected free of surrounding tissues from the clavicle proximally to the carotid bifurcation distally. The common carotid artery was cross-clamped using atraumatic vascular clamps placed at each end of the exposed vessel three minutes after a bolus injection of heparin sulfate (100 U/kg intravenously; Elkins-Simm Inc., Cherry Hill, N.J.) and divided 1 cm proximal to the distal crossclamp. The proximal arterial segment was then everted over curved forceps. After maximal eversion was obtained, a pair of polypropylene stay sutures (7-0) was placed on either side proximally and a second pair placed distally in the lumen-exposed segment. The endarterectomy was then performed beginning 1 cm from the divided end of the everted vessel segment and continued for a measured distance of 1 cm. This procedure involves mechanical removal of the normal intima and a partial thickness of media using forceps and a surgical microscope (32×magnification). Following endarterectomy, the vessel was returned to its normal configuration, and an end-to-end anastomosis performed with 7-0 polypropylene suture and continuous technique under 2.5-fold magnification, and the wound closed in layers.

For morphometric analysis of VLF, sections embedded in paraffin and stained for connective tissue components (collagen, elastin) and with hematoxylin-eosin, were evaluated using a Zeiss Photoscope coupled with image analysis system (Thomas Optical Measurement Systems, Columbus, Ga.) consisting of high resolution (580 lines) CCD microscope camera coupled to a high resolution (700 lines) monitor, an IBM 386 chip, 80 MB computer with high resolution graphics digitablet for image acquisition and storage. Quantitative image analysis was performed using a morphometric software driver (Optimas, Bioscan, Inc., Edmonds, Wash.). Arterial cross-sections were analyzed with respect to the total area of neointimal proliferative lesion and corresponding area of arterial media. For statistical analysis, comparisons between groups were made using the Student's t test (two tailed) for paired and unpaired data.

Figure 4:
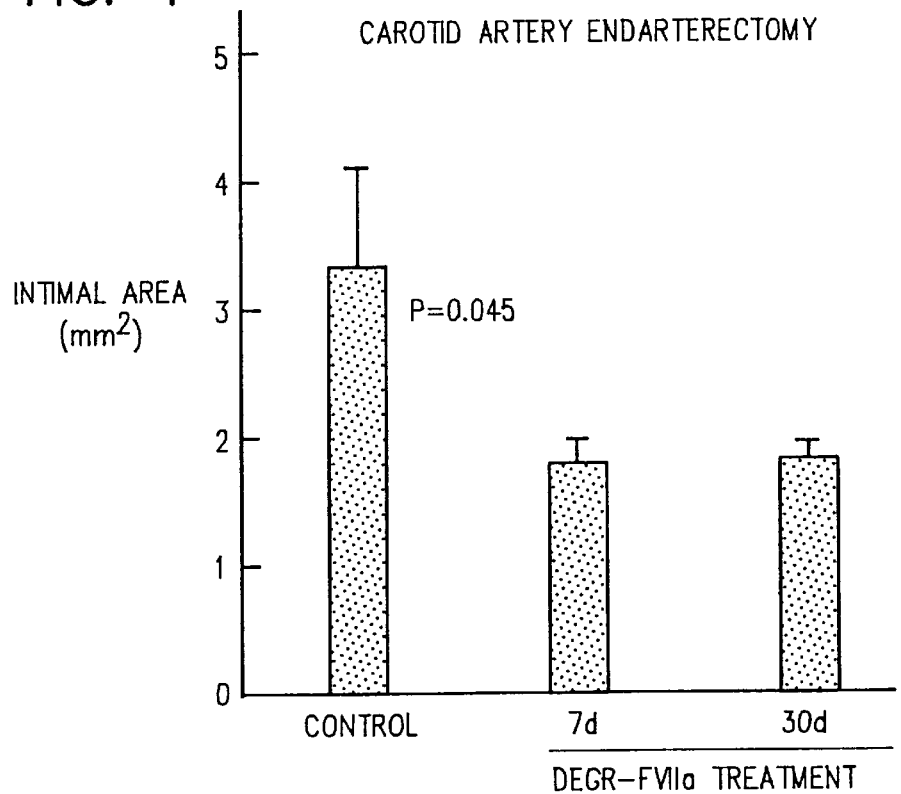
FIG. 4 depicts the size of the intimal area of baboons following carotid artery endarterectomy and treatment with DEGR-Factor VIIa for 7 or 30 days, compared to control animals.

The results showed that the intimal area was significantly decreased in the animals treated with DEGR-Factor VIIa for seven days and studied at 30 days as compared to control animals who had undergone the same vascular injury but who did not obtain any DEGR-Factor VIIa (FIG. 4). A similar result was found in the animal treated with DEGR-Factor VIIa for 30 days and examined at 30 days.

Preliminary studies with a ballon angiographic brachial artery model suggested no measurable benefit of DEGR-Factor VIIa therapy. This model, however, has not been shown in baboons to be a prothrombotic model in which tissue factor plays a key role.

Figure 5:
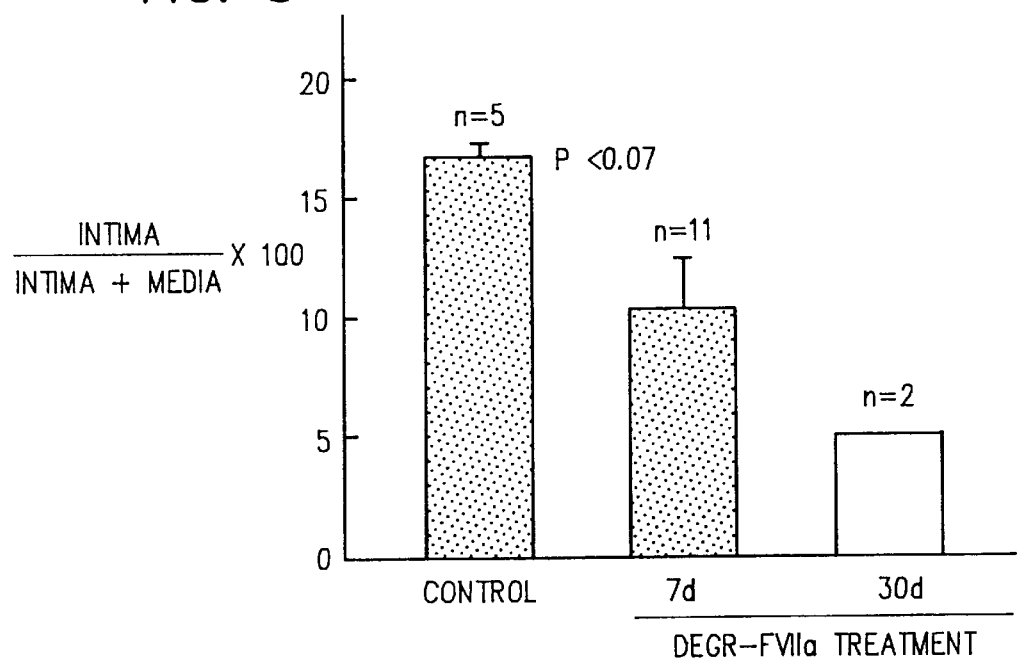
FIG. 5 illustrates the ratio of the intimal area to the intimal+media area of baboon femoral artery following balloon injury and treatment with DEGR-Factor VIIa, where the control group included 5 vessels, 7 day treatment examined 11 vessels, and 30 day treatment examined 2 vessels (n=number of vessels examined).

Studies with the femoral artery balloon injury in the baboon did show a statistically significant benefit from DEGR-Factor VIIa as compared to controls, as shown in FIG. 5.

It is evident from the foregoing that compositions of Factor VII or VIIa having modified catalytic sites are provided which are able to bind tissue factor yet are substantially unable to activate Factors X and IX. As modified Factor VII acts specifically to interrupt the clotting cascade without degrading or consuming clotting factors, administration of modified Factor VII preparations will be accompanied by fewer undesirable side effects than experienced with current therapies. Further, the modified Factor VII described herein may readily be produced by recombinant means. Thus efficacy, convenience and economics of lower dosages and less frequent administration, and a relative lack of toxicity are among the advantages conferred by the compositions of the present invention.

Although the foregoing invention has been described in some detail by way of illustration and example for purposes of clarity of understanding, it will be obvious that certain changes and modifications may be practiced within the scope of the appended claims.

What is claimed is:

1. A method for inhibiting vascular restenosis that is associated with acute vascular injury in an individual, comprising administering to the individual a therapeutically effective amount of a composition which comprises a pharmacologically acceptable Factor VII having at least one covalent modification in its catalytic center, which modification inhibits the ability of the modified Factor VII to activate plasma Factor X or IX.

2. The method of claim 1, wherein the Factor VII modification is produced by reaction of the Factor VII with a serine protease inhibitor.

3. The method of claim 2, wherein the protease inhibitor is an organophosphor compound, a sulfanyl fluoride, a peptide halomethyl ketone, or an azapeptide.

4. The method of claim 3, wherein the protease inhibitor is a peptide halomethyl ketone selected from Dansyl-Phe-Pro-Arg chloromethyl ketone or Dansyl-Glu-Gly-Arg chloromethyl ketone.

5. The method of claim 1, wherein the Factor VII modification comprises at least one amino acid substitution or deletion in a catalytic triad of Ser, Asp, and His.

6. The method of claim 1, wherein the restenosis is secondary to mechanical injury to an artery.

7. The method of claim 6, wherein the mechanical injury is caused by balloon angioplasty, endarterectomy, reductive atherectomy, stent placement, laser therapy or rotablation.

8. The method of claim 6, wherein the composition is administered to the individual within 24 hours prior to the mechanical injury to said artery.

9. The method of claim 6, wherein the composition is further administered to the individual subsequent to the mechanical injury to said artery.

10. The method of claim 1, wherein the restenosis occurs in a vascular graft, stent, bypass graft or organ transplant.

11. The method of claim 10, wherein the composition is administered to the individual within 24 hours prior to placement of said graft, stent, bypass graft or organ transplant.

12. The method of claim 10, wherein the composition is administered to the individual subsequent to placement of said graft, stent, bypass graft or organ transplant.

13. The method of claim 1, comprising further administering to said individual tissue plasminogen activator or streptokinase.

14. The method of claim 1, wherein the Factor VII is human Factor VII.

15. A method for inhibiting vascular restenosis in a patient comprising administering to the patient a therapeutically effective dose of a composition comprising human Factor VII covalently modified in its catalytic center by a protease inhibitor selected from an organophosphor compound, a sulfanyl fluoride, a peptide halomethyl ketone, or an azapeptide, and said modified human Factor VII inhibits the ability of the modified Factor VII to activate human plasma Factor X or IX.

16. The method of claim 15, wherein the protease inhibitor is a peptide halomethyl ketone.

17. The method of claim 15, wherein the modified human Factor VII is administered at the site of the vascular restenosis.

18. The method of claim 15, wherein the modified human Factor VII is administered systemically.

19. The method of claim 15, wherein the modified human Factor VII is administered in an amount from 1 mg to 200 mg.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2422 base pairs
      (B) TYPE: nucleic acid
      (C) STRANDEDNESS: single
      (D) TOPOLOGY: linear (ii) MOLECULE TYPE: cDNA (iii) HYPOTHETICAL: N (iv) ANTI-SENSE: N (ix) FEATURE:
    (A) NAME/KEY: CDS
    (B) LOCATION: 28..1420
    (D) OTHER INFORMATION: /codon_start= 28
        /product= "Factor VII"

(xi) SEQUENCE DESCRIPTION: SEQ ID NO:1:

```
CCTCCCGACA ATACAGGGGC AGCACTGCAG AGATTTCATC ATG GTC TCC CAG GCC         55
                                            Met Val Ser Gln Ala
                                            -38         -35

CTC AGG CTC CTC TGC CTT CTG CTT GGG CTT CAG GGC TGC CTG GCT GCA        103
Leu Arg Leu Leu Cys Leu Leu Leu Gly Leu Gln Gly Cys Leu Ala Ala
        -30                 -25                 -20

GTC TTC GTA ACC CAG GAG GAA GCC CAC GGC GTC CTG CAC CGG CGC CGG        151
Val Phe Val Thr Gln Glu Glu Ala His Gly Val Leu His Arg Arg Arg
        -15                 -10                  -5

CGC GCC AAC GCG TTC CTG GAG GAG CTG CGG CCG GGC TCC CTG GAG AGG        199
Arg Ala Asn Ala Phe Leu Glu Glu Leu Arg Pro Gly Ser Leu Glu Arg
  1               5                  10                  15

GAG TGC AAG GAG GAG CAG TGC TCC TTC GAG GAG GCC CGG GAG ATC TTC        247
Glu Cys Lys Glu Glu Gln Cys Ser Phe Glu Glu Ala Arg Glu Ile Phe
                20                  25                  30

AAG GAC GCG GAG AGG ACG AAG CTG TTC TGG ATT TCT TAC AGT GAT GGG        295
Lys Asp Ala Glu Arg Thr Lys Leu Phe Trp Ile Ser Tyr Ser Asp Gly
                35                  40                  45

GAC CAG TGT GCC TCA AGT CCA TGC CAG AAT GGG GGC TCC TGC AAG GAC        343
Asp Gln Cys Ala Ser Ser Pro Cys Gln Asn Gly Gly Ser Cys Lys Asp
            50                  55                  60

CAG CTC CAG TCC TAT ATC TGC TTC TGC CTC CCT GCC TTC GAG GGC CGG        391
Gln Leu Gln Ser Tyr Ile Cys Phe Cys Leu Pro Ala Phe Glu Gly Arg
        65                  70                  75

AAC TGT GAG ACG CAC AAG GAT GAC CAG CTG ATC TGT GTG AAC GAG AAC        439
Asn Cys Glu Thr His Lys Asp Asp Gln Leu Ile Cys Val Asn Glu Asn
 80                  85                  90                  95

GGC GGC TGT GAG CAG TAC TGC AGT GAC CAC ACG GGC ACC AAG CGC TCC        487
Gly Gly Cys Glu Gln Tyr Cys Ser Asp His Thr Gly Thr Lys Arg Ser
                100                 105                 110

TGT CGG TGC CAC GAG GGG TAC TCT CTG CTG GCA GAC GGG GTG TCC TGC        535
Cys Arg Cys His Glu Gly Tyr Ser Leu Leu Ala Asp Gly Val Ser Cys
            115                 120                 125

ACA CCC ACA GTT GAA TAT CCA TGT GGA AAA ATA CCT ATT CTA GAA AAA        583
Thr Pro Thr Val Glu Tyr Pro Cys Gly Lys Ile Pro Ile Leu Glu Lys
        130                 135                 140

AGA AAT GCC AGC AAA CCC CAA GGC CGA ATT GTG GGG GGC AAG GTG TGC        631
Arg Asn Ala Ser Lys Pro Gln Gly Arg Ile Val Gly Gly Lys Val Cys
    145                 150                 155

CCC AAA GGG GAG TGT CCA TGG CAG GTC CTG TTG TTG GTG AAT GGA GCT        679
Pro Lys Gly Glu Cys Pro Trp Gln Val Leu Leu Leu Val Asn Gly Ala
160                 165                 170                 175

CAG TTG TGT GGG GGG ACC CTG ATC AAC ACC ATC TGG GTG GTC TCC GCG        727
Gln Leu Cys Gly Gly Thr Leu Ile Asn Thr Ile Trp Val Val Ser Ala
                180                 185                 190

GCC CAC TGT TTC GAC AAA ATC AAG AAC TGG AGG AAC CTG ATC GCG GTG        775
Ala His Cys Phe Asp Lys Ile Lys Asn Trp Arg Asn Leu Ile Ala Val
            195                 200                 205

CTG GGC GAG CAC GAC CTC AGC GAG CAC GAC GGG GAT GAG CAG AGC CGG        823
Leu Gly Glu His Asp Leu Ser Glu His Asp Gly Asp Glu Gln Ser Arg
        210                 215                 220

CGG GTG GCG CAG GTC ATC ATC CCC AGC ACG TAC GTC CCG GGC ACC ACC        871
```

```
Arg Val Ala Gln Val Ile Ile Pro Ser Thr Tyr Val Pro Gly Thr Thr
    225                 230                 235

AAC CAC GAC ATC GCG CTG CTC CGC CTG CAC CAG CCC GTG GTC CTC ACT        919
Asn His Asp Ile Ala Leu Leu Arg Leu His Gln Pro Val Val Leu Thr
240                 245                 250                 255

GAC CAT GTG GTG CCC CTC TGC CTG CCC GAA CGG ACG TTC TCT GAG AGG        967
Asp His Val Val Pro Leu Cys Leu Pro Glu Arg Thr Phe Ser Glu Arg
                260                 265                 270

ACG CTG GCC TTC GTG CGC TTC TCA TTG GTC AGC GGC TGG GGC CAG CTG       1015
Thr Leu Ala Phe Val Arg Phe Ser Leu Val Ser Gly Trp Gly Gln Leu
                275                 280                 285

CTG GAC CGT GGC GCC ACG GCC CTG GAG CTC ATG GTC CTC AAC GTG CCC       1063
Leu Asp Arg Gly Ala Thr Ala Leu Glu Leu Met Val Leu Asn Val Pro
            290                 295                 300

CGG CTG ATG ACC CAG GAC TGC CTG CAG CAG TCA CGG AAG GTG GGA GAC       1111
Arg Leu Met Thr Gln Asp Cys Leu Gln Gln Ser Arg Lys Val Gly Asp
            305                 310                 315

TCC CCA AAT ATC ACG GAG TAC ATG TTC TGT GCC GGC TAC TCG GAT GGC       1159
Ser Pro Asn Ile Thr Glu Tyr Met Phe Cys Ala Gly Tyr Ser Asp Gly
320                 325                 330                 335

AGC AAG GAC TCC TGC AAG GGG GAC AGT GGA GGC CCA CAT GCC ACC CAC       1207
Ser Lys Asp Ser Cys Lys Gly Asp Ser Gly Gly Pro His Ala Thr His
                340                 345                 350

TAC CGG GGC ACG TGG TAC CTG ACG GGC ATC GTC AGC TGG GGC CAG GGC       1255
Tyr Arg Gly Thr Trp Tyr Leu Thr Gly Ile Val Ser Trp Gly Gln Gly
                355                 360                 365

TGC GCA ACC GTG GGC CAC TTT GGG GTG TAC ACC AGG GTC TCC CAG TAC       1303
Cys Ala Thr Val Gly His Phe Gly Val Tyr Thr Arg Val Ser Gln Tyr
            370                 375                 380

ATC GAG TGG CTG CAA AAG CTC ATG CGC TCA GAG CCA CGC CCA GGA GTC       1351
Ile Glu Trp Leu Gln Lys Leu Met Arg Ser Glu Pro Arg Pro Gly Val
385                 390                 395

CTC CTG CGA GCC CCA TTT CCC TAG C CCAGCAGCCC TGGCCTGTGG               1396
Leu Leu Arg Ala Pro Phe Pro
400                 405

AGAGAAAGCC AAGGCTGCGT CGAACTGTCC TGGCACCAAA TCCCATATAT TCTTCTGCAG     1456

TTAATGGGGT AGAGGAGGGC ATGGGAGGGA GGGAGAGGTG GGGAGGGAGA CAGAGACAGA     1516

AACAGAGAGA GACAGAGACA GAGAGAGACT GAGGGAGAGA CTCTGAGGAC ATGGAGAGAG     1576

ACTCAAAGAG ACTCCAAGAT TCAAAGAGAC TAATAGAGAC ACAGAGATGG AATAGAAAAG     1636

ATGAGAGGCA GAGGCAGACA GGCGCTGGAC AGAGGGGCAG GGGAGTGCCA AGGTTGTCCT     1696

GGAGGCAGAC AGCCCAGCTG AGCCTCCTTA CCTCCCTTCA GCCAAGCCCC ACCTGCACGT     1756

GATCTGCTGG CCCTCAGGCT GCTGCTCTGC CTTCATTGCT GGAGACAGTA GAGGCATGAA     1816

CACACATGGA TGCACACACA CACACGCCAA TGCACACACA CAGAGATATG CACACACACG     1876

GATGCACACA CAGATGGTCA CACAGAGATA CGCAAACACA CCGATGCACA CGCACATAGA     1936

GATATGCACA CACAGATGCA CACAGATA TACACATGGA TGCACGCACA TGCCAATGCA      1996

CGCACACATC AGTGCACACG GATGCACAGA GATATGCACA CACCGATGTG CGCACACACA     2056

GATATGCACA CACATGGATG AGCACACACA CACCAAGTGC GCACACACAC CGATGTACAC     2116

ACACAGATGC ACACACAGAT GCACACACAC CGATGCTGAC TCCATGTGTG CTGTCCTCTG     2176

AAGGCGGTTG TTTAGCTCTC ACTTTTCTGG TTCTTATCCA TTATCATCTT CACTTCAGAC     2236

AATTCAGAAG CATCACCATG CATGGTGGCG AATGCCCCCA AACTCTCCCC CAAATGTATT     2296

TCTCCCTTCG CTGGGTGCCG GGCTGCACAG ACTATTCCCC ACCTGCTTCC CAGCTTCACA     2356
```

-continued

```
ATAAACGGCT GCGTCTCCTC CGCACACCTG TGGTGCCTGC CACCCAAAAA AAAAAAAAAA      2416

AAAAAA                                                                 2422
```

(2) INFORMATION FOR SEQ ID NO:2:

(i) SEQUENCE CHARACTERISTICS:
        (A) LENGTH: 444 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Ser Gln Ala Leu Arg Leu Leu Trp Leu Leu Gly Leu Gln
-38             -35                 -30                 -25

Gly Cys Leu Ala Ala Val Phe Val Thr Gln Glu Glu Ala His Gly Val
        -20                 -15                 -10

Leu His Arg Arg Arg Arg Ala Asn Ala Phe Leu Glu Glu Leu Arg Pro
    -5                   1                   5                  10

Gly Ser Leu Glu Arg Glu Cys Lys Glu Gln Cys Ser Phe Glu Glu
                15                  20                  25

Ala Arg Glu Ile Phe Lys Asp Ala Glu Arg Thr Lys Leu Phe Trp Ile
                30                  35                  40

Ser Tyr Ser Asp Gly Asp Gln Cys Ala Ser Ser Pro Cys Gln Asn Gly
            45                  50                  55

Gly Ser Cys Lys Asp Gln Leu Gln Ser Tyr Ile Cys Phe Cys Leu Pro
        60                  65                  70

Ala Phe Glu Gly Arg Asn Cys Glu Thr His Lys Asp Asp Gln Leu Ile
75                  80                  85                  90

Cys Val Asn Glu Asn Gly Gly Cys Glu Gln Tyr Cys Ser Asp His Thr
                95                  100                 105

Gly Thr Lys Arg Ser Cys Arg Cys His Glu Gly Tyr Ser Leu Leu Ala
                110                 115                 120

Asp Gly Val Ser Cys Thr Pro Thr Val Glu Tyr Pro Cys Gly Lys Ile
                125                 130                 135

Pro Ile Leu Glu Lys Arg Asn Ala Ser Lys Pro Gln Gly Arg Ile Val
140                 145                 150

Gly Gly Lys Val Cys Pro Lys Gly Glu Cys Pro Trp Gln Val Leu Leu
155                 160                 165                 170

Leu Val Asn Gly Ala Gln Leu Cys Gly Gly Thr Leu Ile Asn Thr Ile
                175                 180                 185

Trp Val Val Ser Ala Ala His Cys Phe Asp Lys Ile Lys Asn Trp Arg
                190                 195                 200

Asn Leu Ile Ala Val Leu Gly Glu His Asp Leu Ser Glu His Asp Gly
                205                 210                 215

Asp Glu Gln Ser Arg Arg Val Ala Gln Val Ile Ile Pro Ser Thr Tyr
                220                 225                 230

Val Pro Gly Thr Thr Asn His Asp Ile Ala Leu Leu Arg Leu His Gln
235                 240                 245                 250

Pro Val Val Leu Thr Asp His Val Val Pro Leu Cys Leu Pro Glu Arg
                255                 260                 265

Thr Phe Ser Glu Arg Thr Leu Ala Phe Val Arg Phe Ser Leu Val Ser
                270                 275                 280

Gly Trp Gly Gln Leu Leu Asp Arg Gly Ala Thr Ala Leu Glu Leu Met
                285                 290                 295
```

```
-continued

Val Leu Asn Val Pro Arg Leu Met Thr Gln Asp Cys Leu Gln Gln Ser
    300             305             310

Arg Lys Val Gly Asp Ser Pro Asn Ile Thr Glu Tyr Met Phe Cys Ala
315             320             325             330

Gly Tyr Ser Asp Gly Ser Lys Asp Ser Cys Lys Gly Asp Ser Gly Gly
            335             340             345

Pro His Ala Thr His Tyr Arg Gly Thr Trp Tyr Leu Thr Gly Ile Val
            350             355             360

Ser Trp Gly Gln Gly Cys Ala Thr Val Gly His Phe Gly Val Tyr Thr
            365             370             375

Arg Val Ser Gln Tyr Ile Glu Trp Leu Gln Lys Leu Met Arg Ser Glu
            380             385             390

Pro Arg Pro Gly Val Leu Leu Arg Ala Pro Phe Pro
395             400             405

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: N (iv) ANTI-SENSE: N (xi) SEQUENCE DESCRIPTION: SEQ ID NO:3:

TGGGCCTCCG GCGTCCCCCT T                                           21

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: N (iv) ANTI-SENSE: N (xi) SEQUENCE DESCRIPTION: SEQ ID NO:4:

TCCCAGTCAC GACGT                                                  15
```